(12) United States Patent
Zamierowski

(10) Patent No.: US 7,108,683 B2
(45) Date of Patent: Sep. 19, 2006

(54) WOUND THERAPY AND TISSUE MANAGEMENT SYSTEM AND METHOD WITH FLUID DIFFERENTIATION

(75) Inventor: David S. Zamierowski, Overland Park, KS (US)

(73) Assignee: KCI Licensing, Inc, San Antonio, TX (US)

( * ) Notice: Subject to any disclaimer, the term of this patent is extended or adjusted under 35 U.S.C. 154(b) by 196 days.

(21) Appl. No.: 10/135,741

(22) Filed: Apr. 30, 2002

(65) Prior Publication Data

US 2003/0050594 A1 Mar. 13, 2003

Related U.S. Application Data

(60) Provisional application No. 60/287,323, filed on Apr. 30, 2001.

(51) Int. Cl.
*A61F 13/00* (2006.01)
*A61F 13/02* (2006.01)

(52) U.S. Cl. ............... 604/304; 604/305; 604/306; 604/307; 604/308

(58) Field of Classification Search ........ 604/304–308, 604/24, 46, 378, 40
See application file for complete search history.

(56) References Cited

U.S. PATENT DOCUMENTS

| 1,335,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,969,057 | A | 1/1961 | Simmons |
| 3,367,332 | A | 2/1968 | Groves |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez |
| 4,165,748 | A | 8/1979 | Johnson |
| 4,233,969 | A | 11/1980 | Lock et al. |
| 4,245,630 | A | 1/1981 | Lloyd et al. |
| 4,261,363 | A | 4/1981 | Russo |
| 4,275,721 | A | 6/1981 | Olson |
| 4,284,079 | A | 8/1981 | Adair |
| 4,297,795 | A | 11/1981 | Golub |
| 4,333,468 | A | 6/1982 | Geist |
| 4,373,519 | A | 2/1983 | Errede et al. |
| 4,382,441 | A * | 5/1983 | Svedman .................. 604/291 |

(Continued)

FOREIGN PATENT DOCUMENTS

AU B-87770/82 8/1982

(Continued)

OTHER PUBLICATIONS

Frank E. Johnson: "An Improved Technique for Skin Graft Placement Using a Suction Drain", Surgery, Gynecology and Obstetrics, 1984, 159(6), pp. 584 and 585.

*Primary Examiner*—Jacqueline F. Stephens

(57) ABSTRACT

A wound therapy and tissue management system utilizes fluid differentiation. Fluid is differentiated by establishing a gradient within the system. A gradient can be established with matter or energy. Patient interfaces for establishing, maintaining and varying one or more gradients include transfer elements with first and second zones having different flow coefficients. The transfer elements exchange fluid with a patient, generally through a wound site, and with external components of the system. Osmotic solution gradients are controlled by a methodology involving the present invention for extracting solutions, which can include toxins, from patients and for introducing fluids and sumping air to wound sites.

21 Claims, 25 Drawing Sheets

U.S. PATENT DOCUMENTS

| | | |
|---|---|---|
| 4,392,853 A | 7/1983 | Muto |
| 4,392,858 A | 7/1983 | George et al. |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vailancourt |
| 4,540,412 A | 9/1985 | Van Overloop |
| 4,543,100 A | 9/1985 | Brodsky |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,733,659 A | 3/1988 | Edenbaum et al. |
| 4,743,232 A | 5/1988 | Kruger |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,100,396 A | 3/1992 | Zamierowski |
| 5,149,331 A | 9/1992 | Ferdman et al. |
| 5,167,613 A | 12/1992 | Karami et al. |
| 5,176,663 A | 1/1993 | Svedman et al. |
| 5,232,453 A | 8/1993 | Plass et al. |
| 5,261,893 A | 11/1993 | Zamierowski |
| 5,298,015 A | 3/1994 | Komatsuzaki et al. |
| 5,344,415 A | 9/1994 | Debusk et al. |
| 5,358,494 A | 10/1994 | Svedman |
| 5,527,293 A | 6/1996 | Zamierowski |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,398,767 B1 * | 6/2002 | Fleischmann ............... 604/313 |
| 6,488,643 B1 | 12/2002 | Tumey et al. |
| 6,493,568 B1 | 12/2002 | Bell et al. |
| 2002/0115951 A1 | 8/2002 | Norstream et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| EP | 0100148 | 2/1984 |

\* cited by examiner

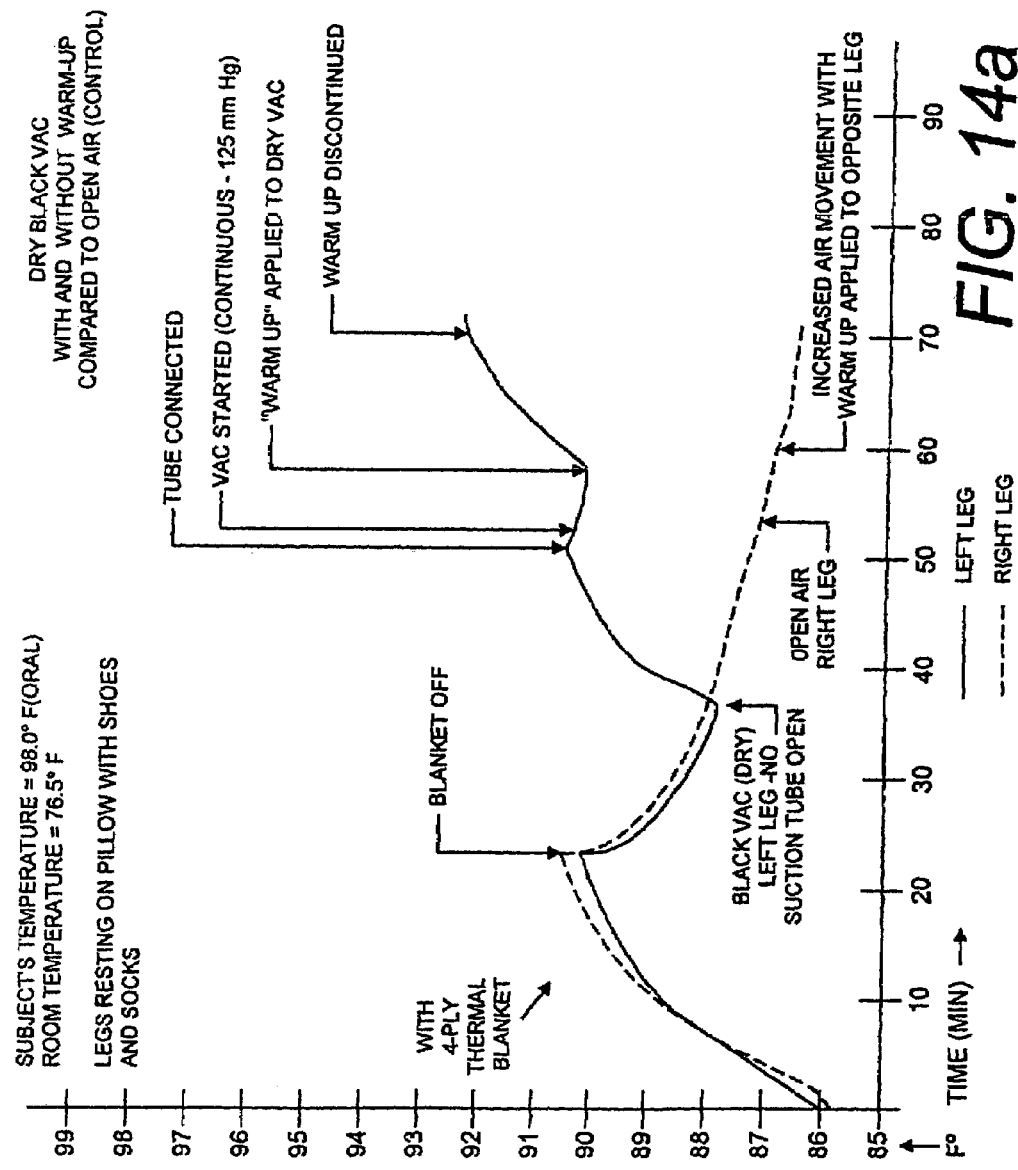

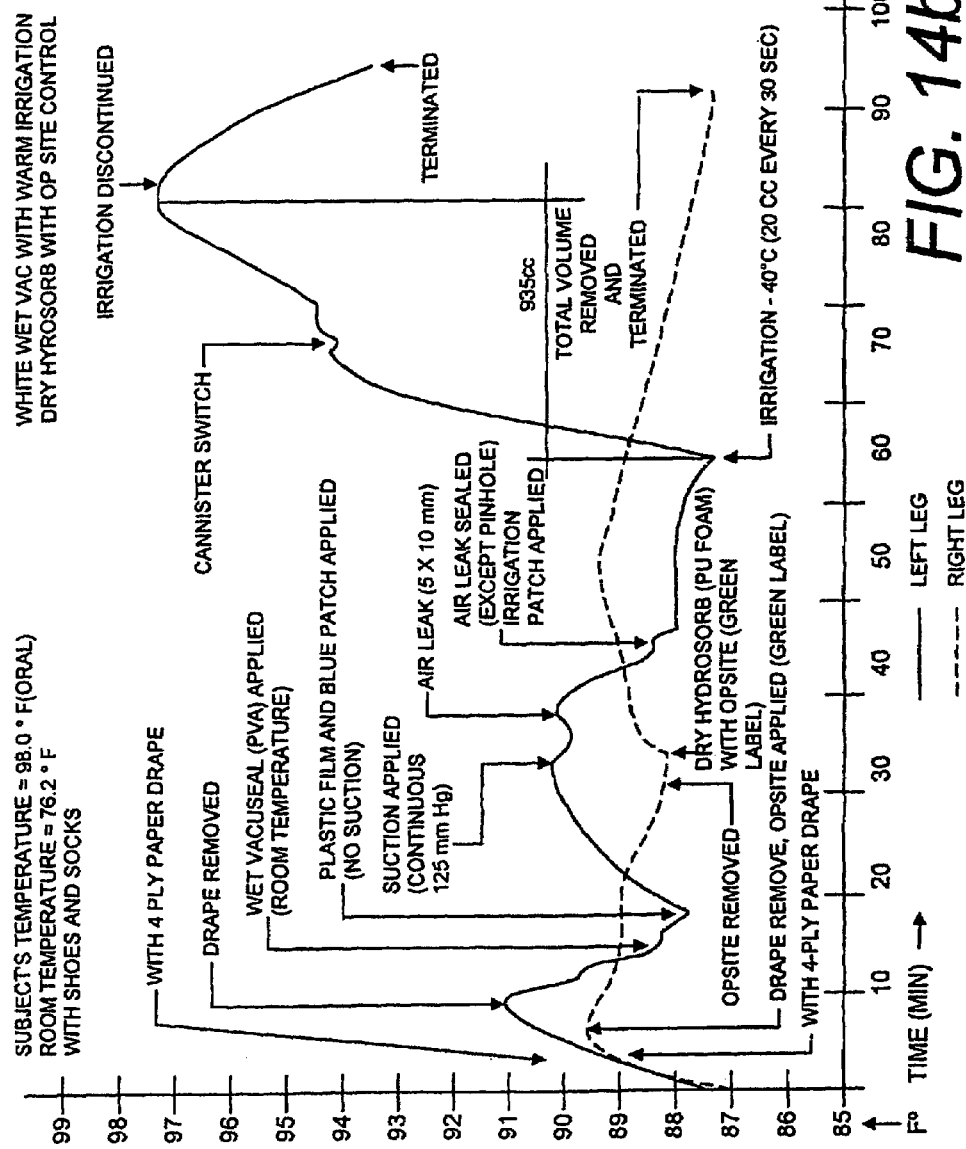

FIG. 21

HYPO-OSMOLAR OR HEAVY DRAPE SYSTEM

| PHASE: | 1 | 2 | 3 | 4 |
|---|---|---|---|---|
| TRANSFER ELEMENT | ← | HYPO-OSMOLAR | ↓→ FLUID | |
| WOUND | FLUID TOXIN A | ↔ FLUID TOXIN A → | FLUID TOXIN A | FLUID ↑ TOXIN A ↔ |
| CAPILLARY | → | | | LYMPHATICS |

WOUND THERAPY AND TISSUE MANAGEMENT SYSTEM AND METHOD WITH FLUID DIFFERENTIATION

CROSS-REFERENCE TO RELATED APPLICATION AND PRIORITY CLAIM

The present application is based on and claims priority in U.S. Provisional Patent Application Ser. No. 60/287,323; filed Apr. 30, 2001.

BACKGROUND OF THE INVENTION

1. Field of the Invention

The present invention relates generally to medical care, and in particular to wound therapy and tissue management systems and methodologies with fluid differentiation.

2. Description of the Prior Art

Heretofore, many wound therapy and tissue management devices and protocols have tended to focus on the addition or control of individual mechanical forces and their respective effects on wound healing. For example, the use of suction to secure skin graft dressings in place is disclosed in Johnson, F. E., *An Improved Technique for Skin Graft Placement Using a Suction Drain;* Surgery, Gynecology and Obstetrics 1984; 159 (6): 584–5. Other prior art devices have focused on the application of compressive (i.e. positive or greater-than-atmospheric) pressure to a wound site, the application of heat and the delivery of pharmacologic agents.

Standard methods in the current practice of wound care require changing the dressing in order to topically add pharmacological agents, which require interval reapplication. Reapplications of pharmacological agents can be minimized or eliminated by using slow-release delivery systems. However, such systems must generally be changed in their entireties in order to change the agents or dosages.

Another wound treatment protocol option involves dosing the entire patient. Agents are thereby delivered systemically, i.e. from within the patient, in order to arrive at the wound site, as opposed to other protocols which deliver respective agents externally or topically. However, systemic medications are generally administered in relatively high doses in order to provide sufficient concentrations in affected areas and treatment sites. Non-affected tissues and organs remote from the treatment sites thus tend to receive concentrations of medications from which they may not benefit.

Fluid management significantly affects many aspects of health care and is involved in many medical procedures. For example, wound care typically involves absorbing and/or draining wound exudates, blood, serum and other body fluids from the patient. Surgical procedures often create wounds requiring tissue management and fluid drainage. For example, skin grafts have exudates and bleeding that require management at both the donor and graft sites. However, current tissue management and fluid drainage procedures are often ineffective in maintaining optimum moisture content for promoting wound healing. Excessive drying, on the other hand, can lead to desiccation, eschar formation and slowing of cell migration. Excessive moisture, on the other hand, can lead to maceration, bacterial overgrowth, tissue breakdown and necrosis.

Various types of porous, absorbent dressing materials have been used for dressing wounds to accumulate body fluids. The dressing materials facilitate drainage and also the collection and disposal of fluids. A disadvantage with many conventional dressings is that they require changing in order to reduce the risk of infection and to maintain effectiveness. However, dressing changes can add significantly to treatment costs and are associated with patient discomfort and medical risks such as infection and damage to reepithelialized tissues. Accordingly, vacuum sources have been employed to drain wounds. For example, Zamierowski U.S. Pat. Nos. 4,969,880; 5,100,396; 5,261,893; 5,527,293 and 6,071,267 pertain to wound dressings, fluid connections, fastening systems and medical procedures utilizing same in connection with vacuum-assisted wound drainage, and are incorporated herein by reference.

A wound drainage device using a hand-operated suction bulb is shown in the George et al. U.S. Pat. No. 4,392,858. Motorized suction pumps can be employed to provide consistent, sub-atmospheric vacuum pressure for maintaining an effective drainage flow. The Richmond et al. U.S. Pat. Nos. 4,655,754 and 4,826,494 disclose vacuum wound drainage systems which can be connected to motorized vacuum pumps.

Another important objective in designing an effective wound drainage system is to provide an effective interface with the patient. Ideally, the patient interface should accommodate various types of wounds in different stages of recovery for as broad a range of applications as possible. As noted above, optimum wound healing generally involves maintaining a sufficient moisture level to avoid desiccation without causing the wound to macerate from excessive moisture. Sufficient moisture levels are required for epithelial cell migration, but excessive moisture can inhibit drying and maturation of the epithelial layer. Pressures should be sufficient for effective drainage without creating excessive negative forces, which could cause pressure necrosis or separate freshly-applied skin grafts.

Wound treatment procedures can also include infusing wound sites with liquids to flush contaminants, counter infection, promote healing growth and anesthetize the wound. Prior art fluid delivery systems include a device for treating tissues disclosed in the Svedman U.S. Pat. No. 4,382,441; a product and process for establishing a sterile area of skin disclosed in the Gross U.S. Pat. No. 3,367,332; and the transderman infusion device disclosed in the Westin U.S. Pat. No. 4,605,399. Equipment has also been available which flushes and collects contaminants from wounds.

Heretofore, there has not been available a system or methodology that allowed the manipulation of multiple mechanical forces affecting wound surfaces. Moreover, there has not previously been available a system or methodology that manipulated the gradients of gases, solids, liquids and medications in such a way as to provide the medical practitioner with various options for delivering various agents either systemically from the patient side or topically from the external side of a wound. Further, there has not been available a system or methodology which affected the removal of toxins and undesirable byproducts by an external egress with the advantages and features of the present invention. Such advantages include minimizing or eliminating dressing changes whereby patient discomfort and infection risks are correspondingly reduced.

Effective control of fixation, temperature, pressure (and its associated gradients for vital gases such as oxygen), osmotic, and oncotic forces, electrical and electromagnetic fields and forces and the addition and/or removal of various nutrients and pharmacological agents have not been achievable with the previous systems and methodologies. Still further, there has not been available a wound treatment system and methodology utilizing a transfer element for the manipulation of gas and liquid pathways under the control of preprogrammed, coordinated influx and efflux cycles. Such cycles are designed to maintain the desired integrity and stability of the system while still allowing variations in multiple forces, flows and concentrations within tolerated ranges. The previous wound treatments also tended to lack the dynamic and interactive features of the present invention whereby various gradients can be adjusted in response to patient wound site conditions. Such gradient adjustments can be accomplished with the present invention through the use of biofeedback loops and patient-responsive sensors.

Osmotic and concentration gradients provide an important mechanism for transferring various elements within the scope of the present invention. Such gradients occur naturally in living organisms and involve the movement of solutes from solutions with greater concentrations to solution with lesser concentrations through semi-permeable membranes. Osmosis is the tendency of solids to pass through semi-permeable membranes into solutions of higher concentrations in order to achieve osmotic equilibrium. Diffusion occurs from an area of higher concentration or partial pressure to an area of lower concentration even without membrane separation. Examples include the diffusion transfer of oxygen from alveoli to capillaries within the lung and the osmotic transfer of toxins and waste within the kidneys from capillaries to tubules and on to the bladder. The systems and methods of the present invention utilize and control osmotic and diffusion gradients to advantage in treating wounds, particularly in connection with the removal of toxins and solution from wound sites by controlling fluids. The control of fluids originates both internally and externally. For example, wound exudates originate internally. External control fluids include sumped air, irrigation, etc.

Previous would treatment systems and methodologies did not provide medical practitioners with the range of options available with the present invention for treating various patient circumstances and conditions.

SUMMARY OF THE INVENTION

In the practice of the present invention, a wound therapy and tissue management system is provided, which includes a collector assembly for attachment to a patient, a transfer assembly connected to the collector assembly and a gradient (e.g., negative pressure/vacuum, positive pressure, temperature, oxygen, etc.) source connected by tubing to the transfer assembly. The system is adaptable for use with various dressing assemblies, including multiple layers and components comprising hydrophobic and hydrophilic foam and sponge materials, semi-permeable and impermeable membranes applied as drapes, transfer system conduits and buffers, and tubular connections to pumps. Alternative embodiments of the system utilize osmotic gradients for controlling transfers and provide various optional configurations with internal and external inputs, installation ports and other components. In the practice of the method of the present invention, a fluid differentiation wound therapy and tissue management method is disclosed, which includes steps of shaping and applying a first sponge comprising a first sponge material to a wound area, applying a first drape, shaping and applying a second sponge comprising a second sponge material on top of the first drape and the first sponge, forming a fluid conduit and connecting same to the second sponge and to a buffer for ultimate connection to a vacuum pump. The conduit and the buffer are also draped. Osmotic wound therapy and tissue management methodologies are also disclosed in connection with the present invention. The transfer of fluids and substances such as toxins can be controlled through the application of such methodologies.

BRIEF DESCRIPTION OF THE DRAWINGS

FIGS. 14a–d comprise graphs showing the temperature-elevating performance of the wound treatment systems shown in FIGS. 11–13.

FIG. 21 is a diagram showing a hypo-osmolar or heavy drape system embodying the present invention.

DETAILED DESCRIPTION OF THE PREFERRED EMBODIMENTS

I. Introduction and Environment

Figure 1:
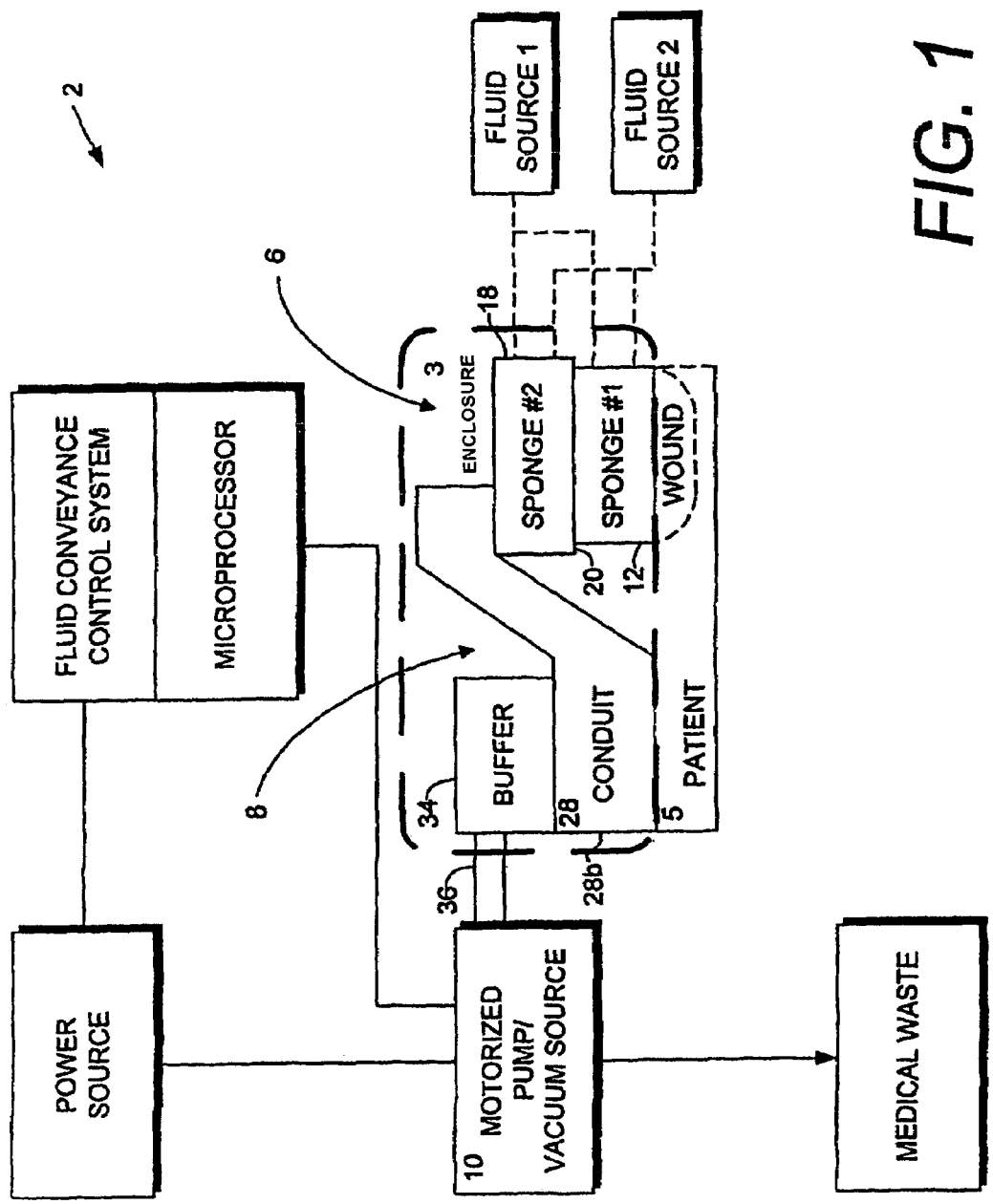
FIG. 1 is a block diagram of a vacuum-fixed wound therapy system embodying the present invention.
Figure 2:
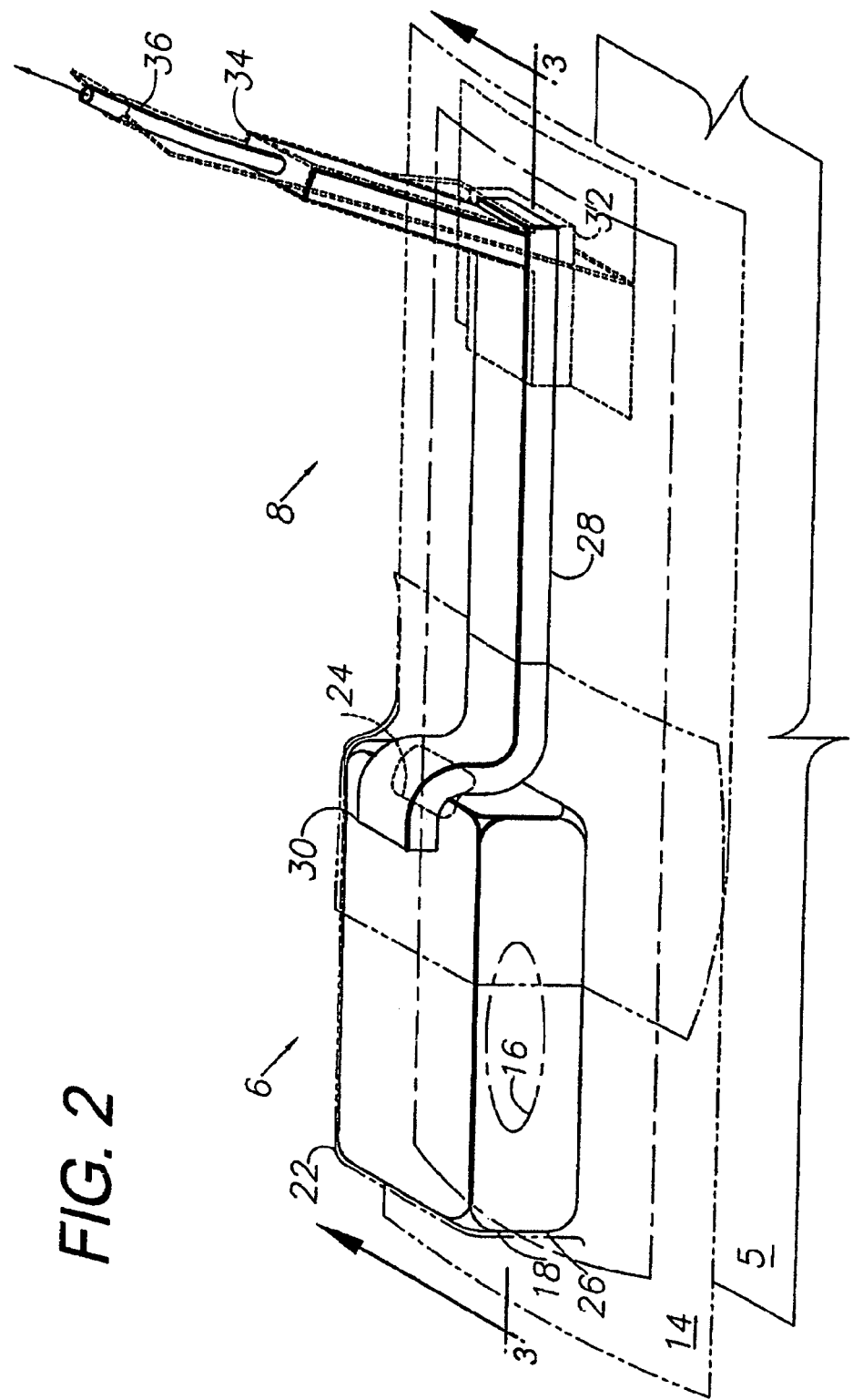
FIG. 2 is a perspective view of a composite dressing assembly.
Figure 3:
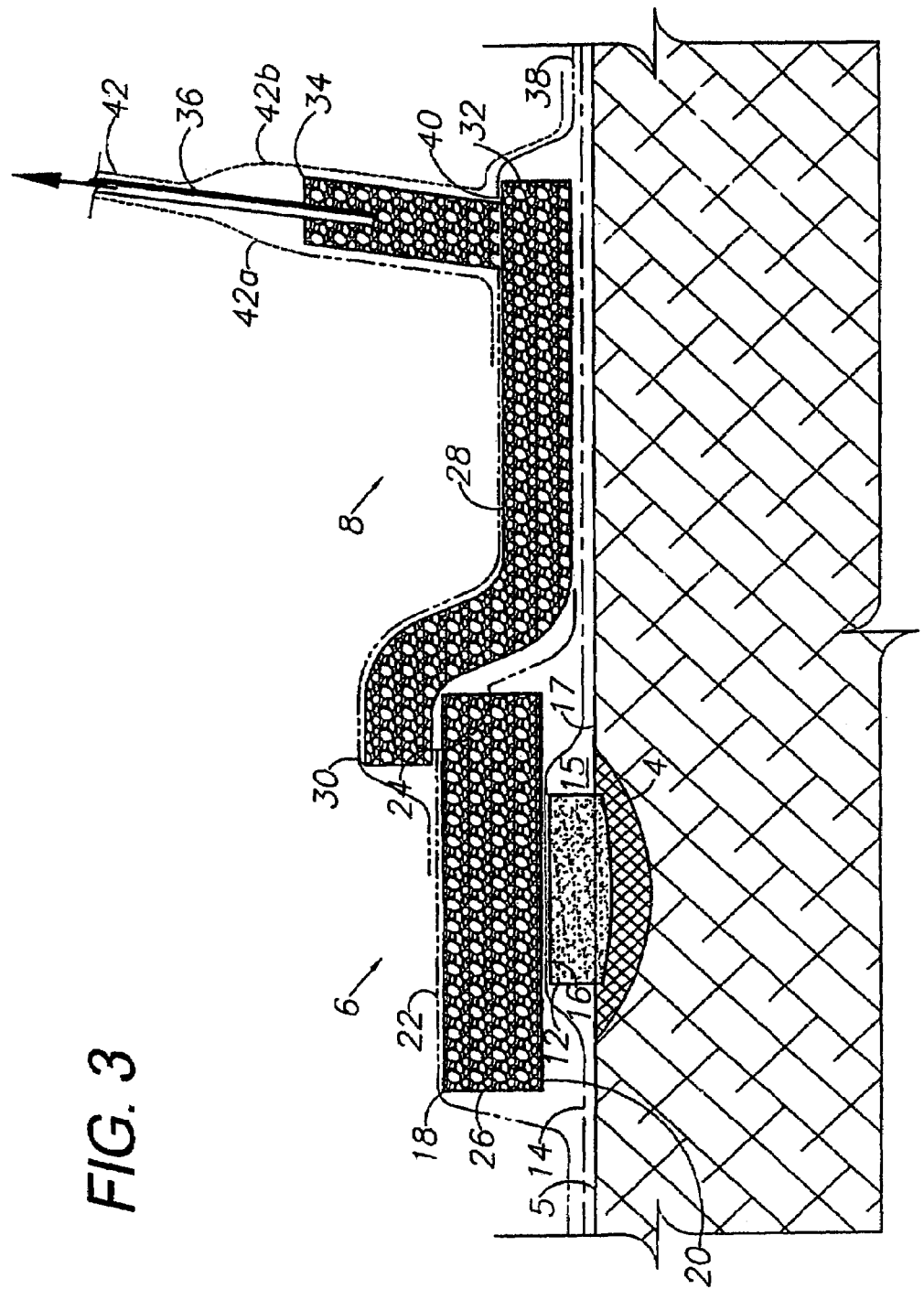
FIG. 3 is a vertical cross-sectional view of the dressing assembly taken generally along line 3—3 in FIG. 2.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Vacuum-Fixed Wound Therapy Dressing 3

Referring to the drawings in more detail, the reference numeral 2 generally designates a vacuum-fixed wound therapy system for application to a wound 4 on or in a patient 5. The system 2 includes an improved dressing 3. Other components of the system 2 are described in my U.S. Pat. No. 6,071,267, which is incorporated herein by reference.

The dressing 3 generally includes a collector assembly 6 and a transfer assembly 8 connected to a vacuum source 10. The collector assembly 6 includes a first sponge 12 comprising a hydrophilic material, such as polyvinyl alcohol (PVA). The first sponge 12 is cut to generally conform to the size of the wound 4. A first sponge drape 14 is placed over the first sponge 12 and an opening 16 is formed in the drape 14 and is preferably sized smaller than the first sponge 12. The drape 14 encloses a compression chamber 15 containing the first sponge 12. A dry skin, moisture-control zone 17 is formed around the first sponge 12 due to air circulation within the compression chamber 15 and promotes healing.

A second sponge 18, preferably comprising a hydrophobic polyurethane ether (PUE) material is sized larger than the first sponge 12, whereby a second sponge overhang 20 extends beyond the perimeter of the first sponge 12. A second sponge drape 22 is placed over the second sponge 18 and includes an opening 24 located along an outer edge 26 of the second sponge 18 for directing the outflow of fluid effluent from the collector assembly 6.

The transfer assembly 8 includes a conduit 28, which can comprise the same hydrophobic material as the second sponge 18. The conduit 28 includes an inlet end 30 which is offset in order to overlie the second sponge drape opening 24 along the second sponge outer edge 26. A conduit outlet end 32 mounts a buffer 34, which also preferably comprises the hydrophobic foam and projects outwardly from the conduit 28 and receives a suction tube 36 which is also connected to the vacuum source (e.g., pump) 10. A conduit drape 38 overlies the conduit 28 and includes an opening 40, which receives the buffer 34. A buffer drape 42 includes a first panel 42a and a second panel 42b, which are secured together over the buffer 34 and the suction tube 36 to enclose same. The buffer drape first and second panels 42a,b are mounted on the conduit drape 38 around the opening 40 therein.

In operation, the hydrophilic first sponge 12 tends to collapse under negative pressure. Therefore, the size of the first sponge 12 is limited and it is preferably mounted in proximity to an edge 26 of the second sponge 18. The second sponge 18 cooperates with the transfer assembly to distribute the negative pressure throughout the hydrophobic second sponge 18 and in turn throughout the first sponge 12. The PVA material comprising the first sponge 12 permits it to compress under a negative pressure gradient. Moreover, because the fluid travel distance in the first sponge 12 tends to be relatively short due to its composition, the overlying second sponge 18 tends to distribute the negative pressure gradient relatively evenly across substantially the entire area of the first sponge 12.

The PUE composition of the second sponge 18 provides a retriculated latticework or weave which resists compression and includes relatively open passages to facilitate fluid flow. Although such open-lattice construction has operational advantages, the passages formed thereby in the second sponge 18 tend to receive "spicule" penetrations from the wound, which is undesirable in many applications. Therefore, the collector assembly 6 is constructed by first forming the first sponge 12 to generally conform to the wound 4, whereafter the second sponge 18 is formed to provide the overhang 20. The first sponge 12 is covered with the first sponge drape 14, the opening 16 of which is normally sized smaller than the overall area of the first sponge 12.

The functional advantages of the collector assembly 6 construction include optimizing compression and fixation and edema control at the wound edge while maximizing the air-induced drying of the intact skin in the dry skin zone 17. Moreover, collector assemblies and transfer assemblies can be mixed and configured in a wide variety of arrangements to accommodate various patient conditions. For example, multiple transfer assemblies 8 can be connected to a single collector assembly 6 and vice versa.

III. First Modified Embodiment Fluid Differentiating Wound Dressing 53

Figure 4:
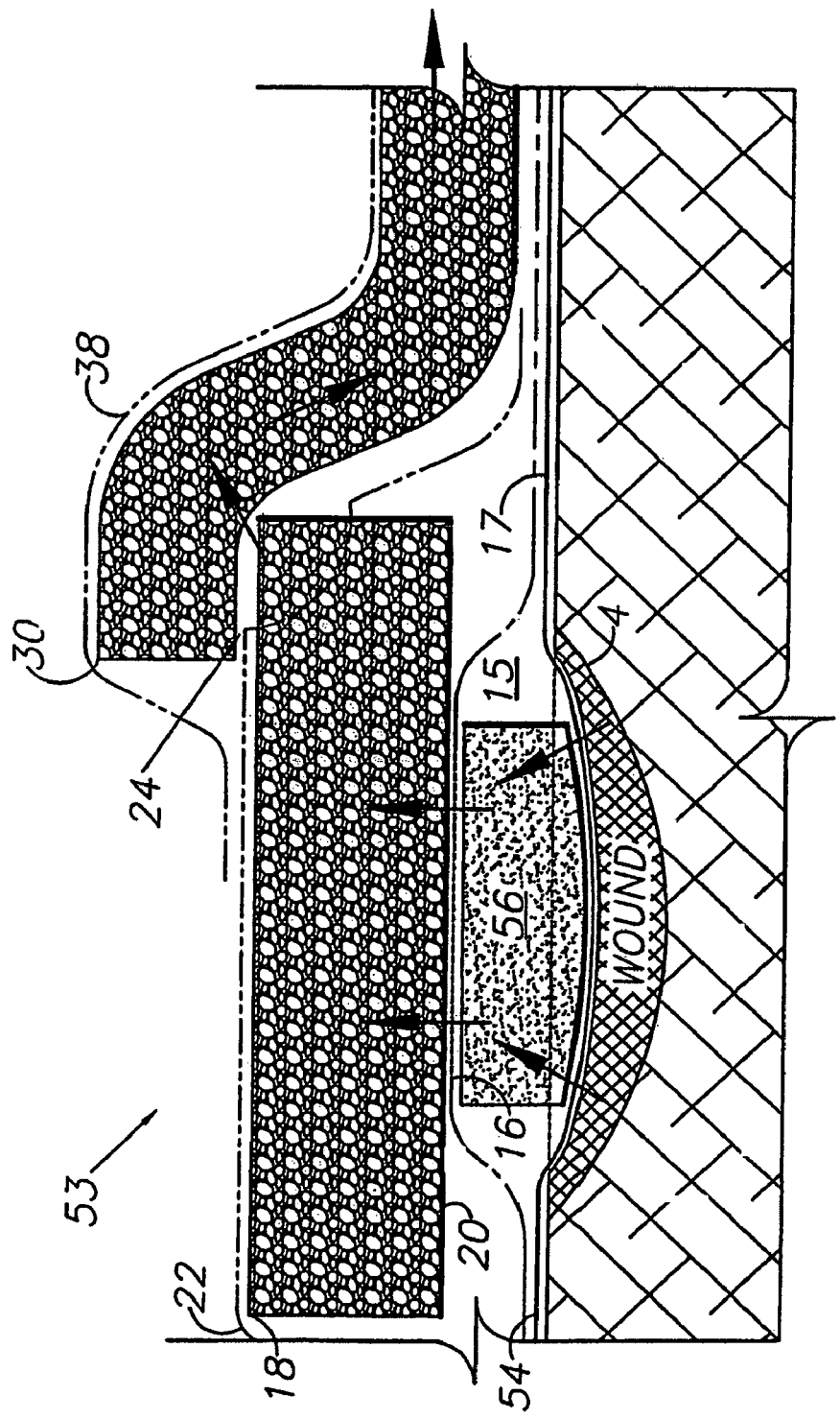
FIG. 4 is an enlarged, fragmentary, cross-sectional view of a composite dressing comprising a first modified embodiment of the present invention.

A wound dressing 53 comprising a first modified embodiment of the present invention is shown in FIG. 4 and includes a liner 54 between the wound 4 and a first sponge 56, which can comprise a hydrophilic or hydrophobic material. The liner 54 passes fluid, but partially isolates and shields the wound tissue from the first sponge 56 to prevent the formation of spicules penetrating the open-passage first sponge 56. The liner 54 thus permits the first sponge 56 to comprise hydrophobic (e.g., PUE) material, even when spicule penetration is not desired.

IV. Second Modified Embodiment Fluid Differentiating Wound Dressing 102

Figure 5:
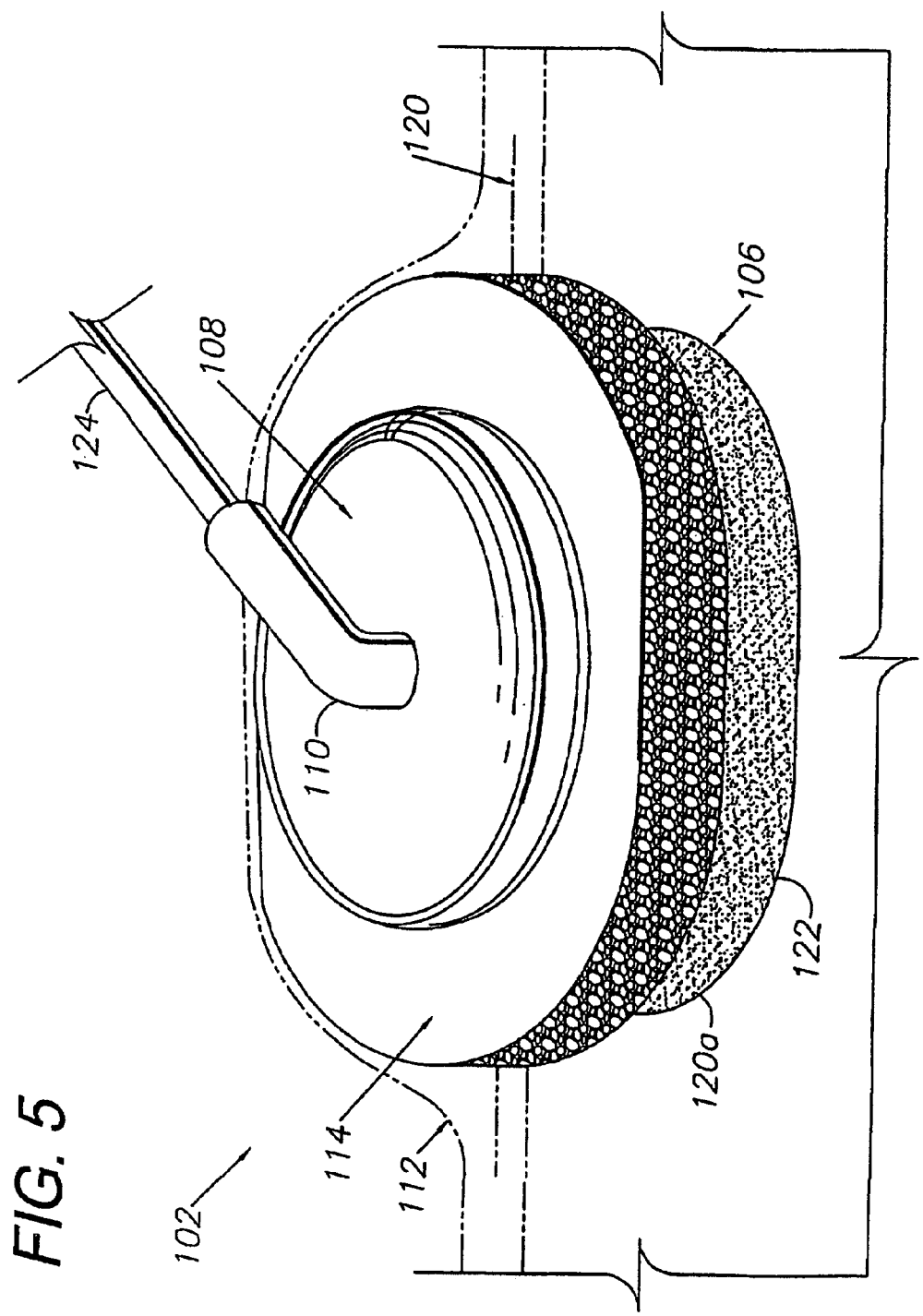
FIG. 5 is a perspective view of a composite dressing comprising a second modified embodiment of the present invention.

A wound dressing comprising a second modified embodiment of the present invention is shown in FIG. 5 and generally comprises a collector assembly 106 and a transfer assembly 108. The collector assembly 106 can be similar to the collector assembly 6 with a suitable composite construction. The transfer assembly 108 comprises an elbow connector 110 placed on top of a second sponge drape 112 covering the second sponge 114. The elbow connector 110 mounts the distal end 116 of a suction tube 118, which is also connected to a vacuum source 10. A first sponge drape 120 is placed over a first, hydrophilic sponge 122 and includes a central opening 123 communicating with the second sponge 114.

Figure 5A:
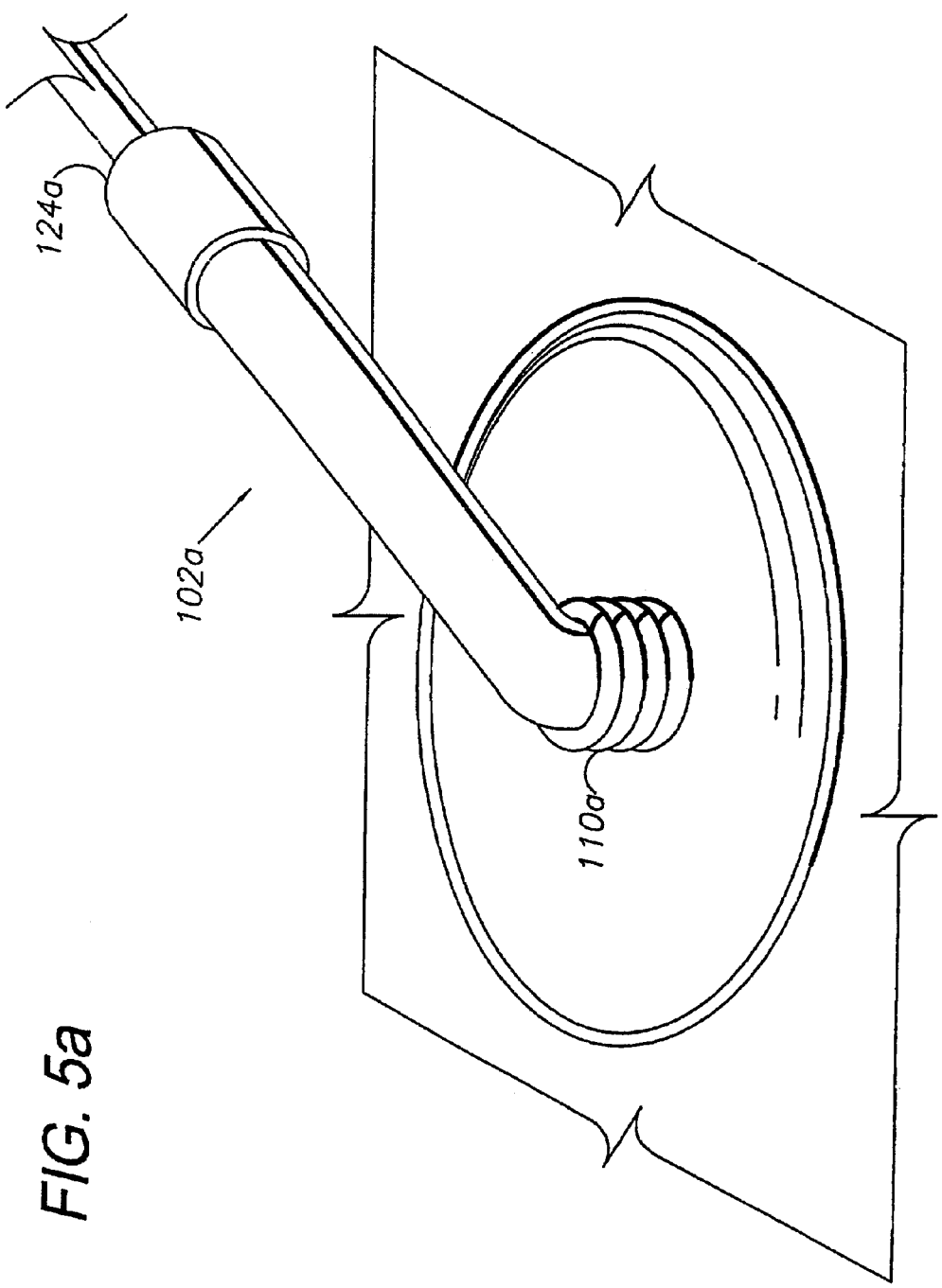
FIG. 5a is a perspective view of a variation of the embodiment shown in FIG. 5.

FIG. 5a shows an interface device 102a comprising a variation of the construction of the wound dressing 102. The device 102a utilizes a flexible, bellows-type tubing section 110a in place of the elbow connector 110 described above. A needle-free, leur lock hub 124a is mounted on the end of the tubing section 110a and functions as an injection port. It will be appreciated that the sponge 122 can be omitted from the dressing 102a whereby same can be used as a fluid inlet or outlet in various applications and on many different configurations of dressings.

V. Third Modified Embodiment Fluid Differentiating Wound Dressing 202

Figure 6:
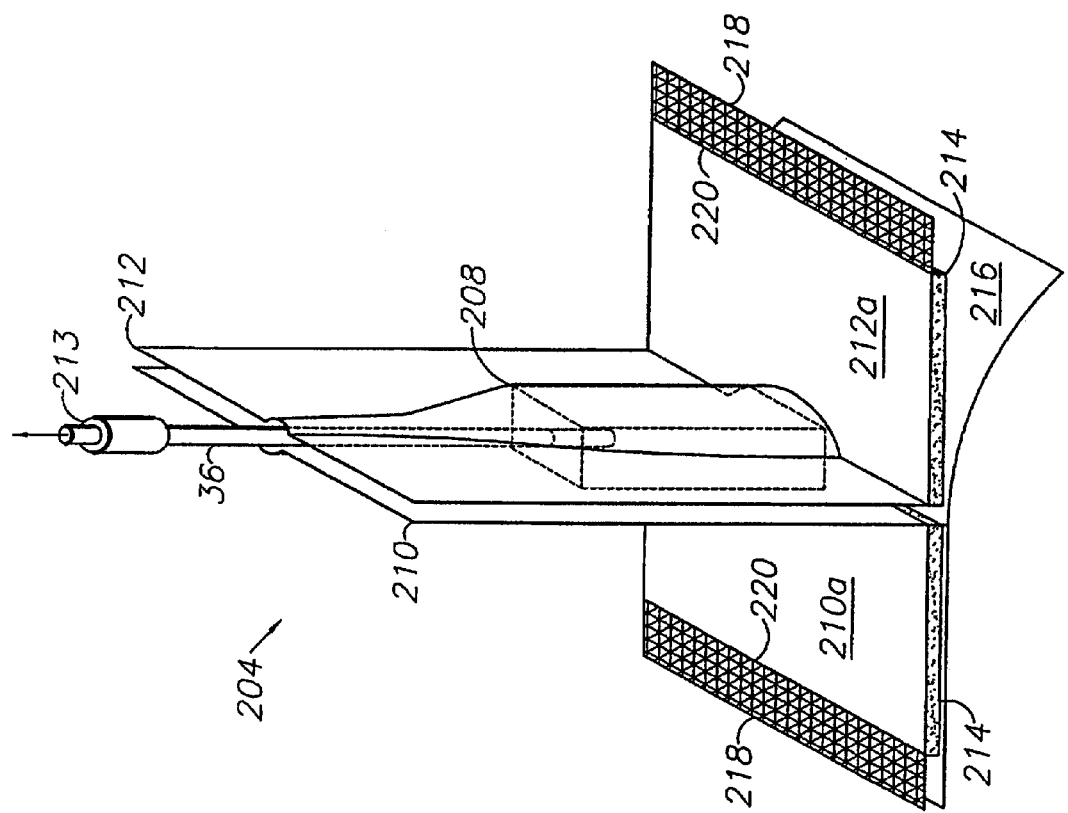
FIG. 6 is a perspective view of a transfer assembly for a composite dressing comprising a third modified embodiment of the present invention.
Figure 7:
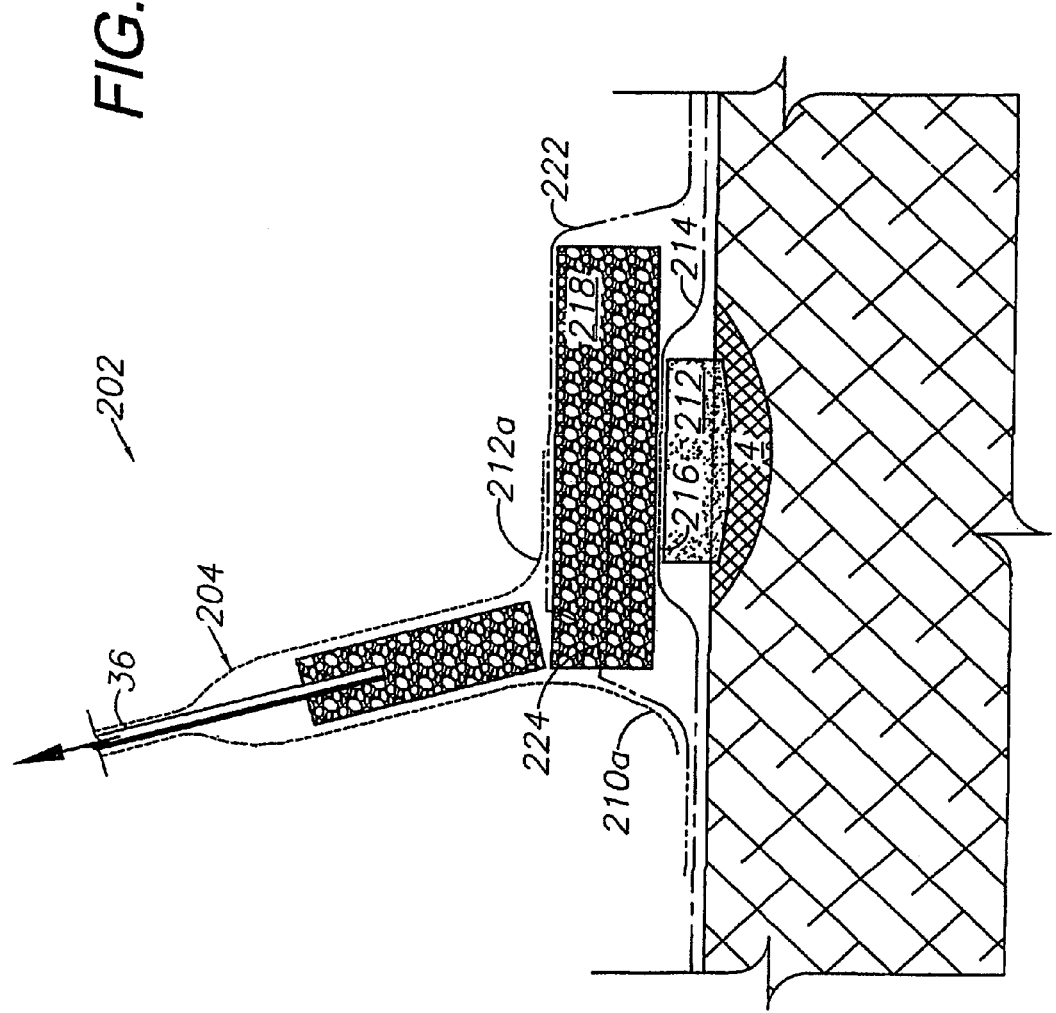
FIG. 7 is a cross-sectional view of a third modified embodiment composite dressing.
Figure 8:
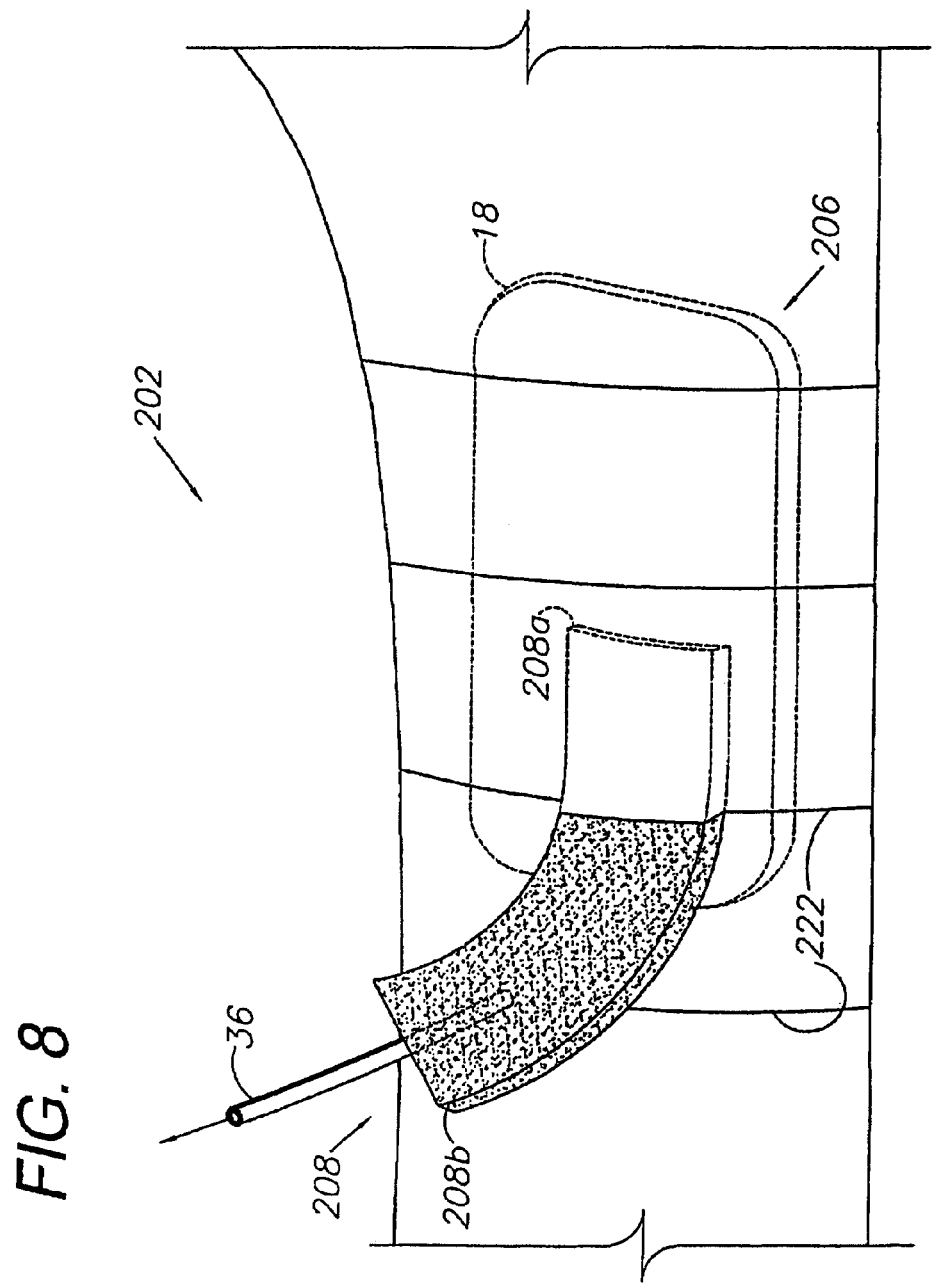
FIG. 8 is a perspective view of the third modified embodiment composite dressing.

A fluid differentiating wound dressing 202 comprising a third modified embodiment of the present invention is shown in FIGS. 6–8 and generally comprises a transfer assembly 204 (FIG. 6) adapted for mounting on a collector assembly 206 as shown in FIG. 7.

The transfer assembly 204 comprises a sponge material buffer 208 which can comprise, for example, polyurethane ether (PUE). The buffer 208 is encased in first and second drape panels 210, 212 with wings 210a, 212a respectively extending in opposite directions from the buffer 208. The wings 210a, 212a have an adhesive layer 214, which is covered by a removable backing sheet 216 prior to installation. Tab strips 218 are provided at the ends of the drape wings 210a, 212a. The tab strips 218 are attached by perforated lines 220 for easy removal upon installation. The suction tube 36 is embedded in the buffer 8 and extends outwardly from the transfer assembly 204 from between the first and second drape panels 210, 212. An optional leur-lock hub to 13 is mounted on the end of the tube 36 for injection port applications.

The transfer assembly 204 is adapted for mounting on a collector assembly 206 (FIG. 7), which is similar to the collector assembly 6 described above. An opening 224 is formed in a second drape 222 which overlies a second sponge 218. With the backing sheet 216 peeled away, the adhesive layer 214 on the drape panel wings 210a, 212a secures the transfer assembly 204 in place whereby the buffer 208 is in communication with the second sponge 218 through the opening 224. An optional first sponge 212 can be placed on the wound 4 and covered with drape 214 with an opening 216 formed therein. The dressing 202 can also be utilized with a single sponge for the collector assembly 206.

FIG. 8 shows an application of the dressing 202 wherein the transfer assembly 204 is mounted over a medial or interior portion 218a of the second sponge 218. A first end 208a of the buffer 208 can be folded substantially flat on top of the second drape which overlies the second sponge 18. A second end 208b of the buffer 208 extends outwardly from the collector assembly 206. The buffer 208 can flex in response to pulling forces tugging on the suction tube 236. The dressing 202 as shown in FIG. 8 is wrapped with drape strips 222, which are adapted for encircling an extremity of a patient. Thus, the buffer first end 208a is secured by a drape strip 222 as shown. The drape strips 222 can be utilized for applying a compressive force to the dressing 202. In operation, evacuating the dressing 202 causes portions of it to shrink, compress and collapse under the pressure gradient, thus providing a visual indication of its performance.

VI. Fourth Modified Embodiment Fluid Differentiating Wound Dressing 302

Figure 9:
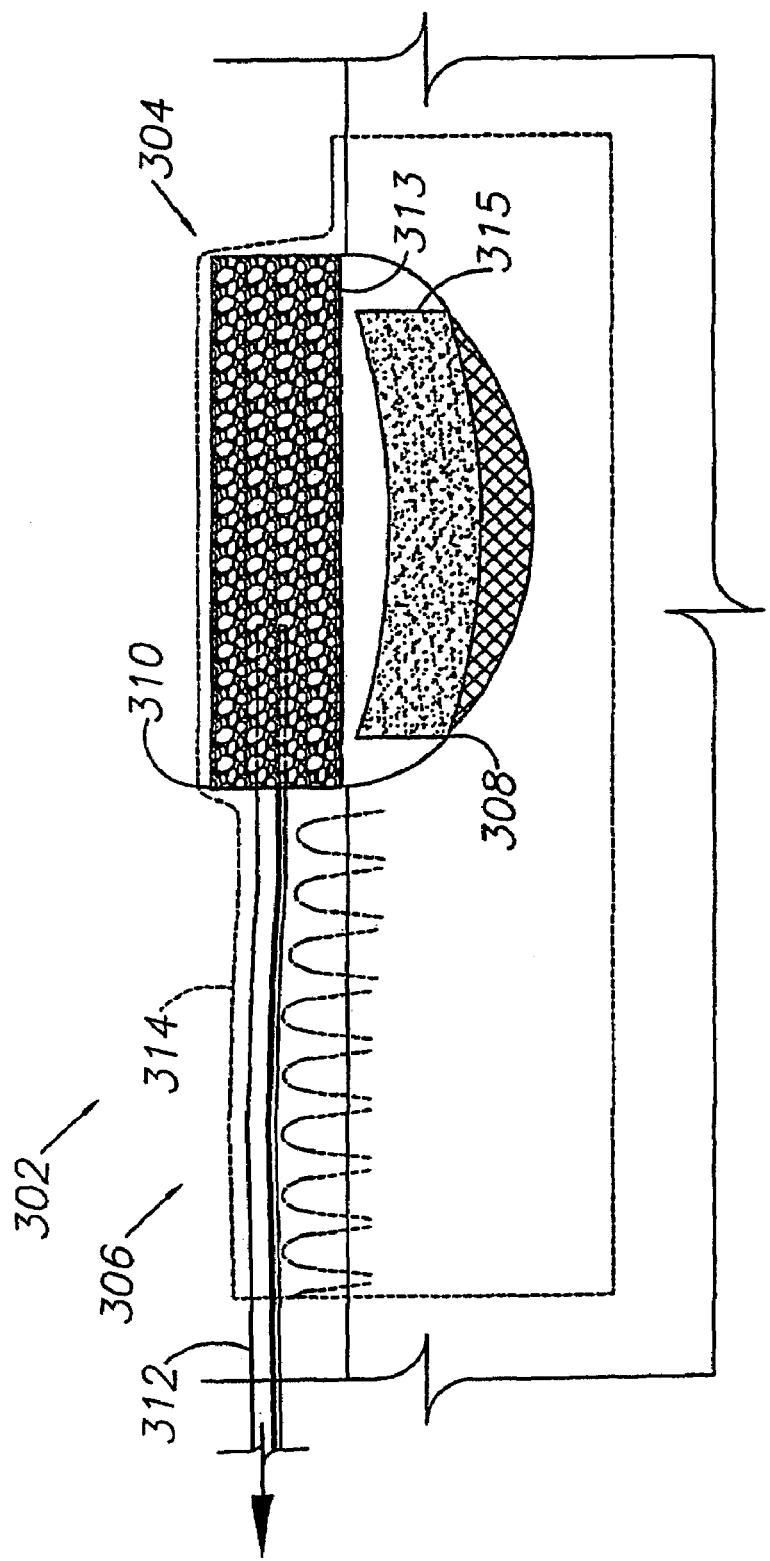
FIG. 9 is a perspective view of a composite dressing comprising a fourth modified embodiment of the present invention.

FIG. 9 shows a fluid differentiating wound dressing 302 comprising a fourth modified embodiment of the present invention. The dressing 302 includes a collector assembly 304 and a transfer assembly 306. The collector assembly 304 includes first and second sponges 308, 310. The first sponge 308 is mounted on the wound and can comprise, for example, a hydrophilic foam material as described above. The second sponge 310 can be mounted directly on the first sponge 308 (optionally separated by a drape) and can receive a tube 312 connected to a vacuum source. The second sponge 310 can include an overhang 313 extending beyond the first sponge 308 for providing a compression chamber 315 as described above. A drape 314 is placed over the collector assembly 304 and the tube 312. The drape 314 is folded over the tube 312 whereby same is spaced outwardly from the skin, thus providing an effective, fluid-tight seal around the tube 312.

VII. Vacuum-Fixed Wound Therapy Method

Figure 10:
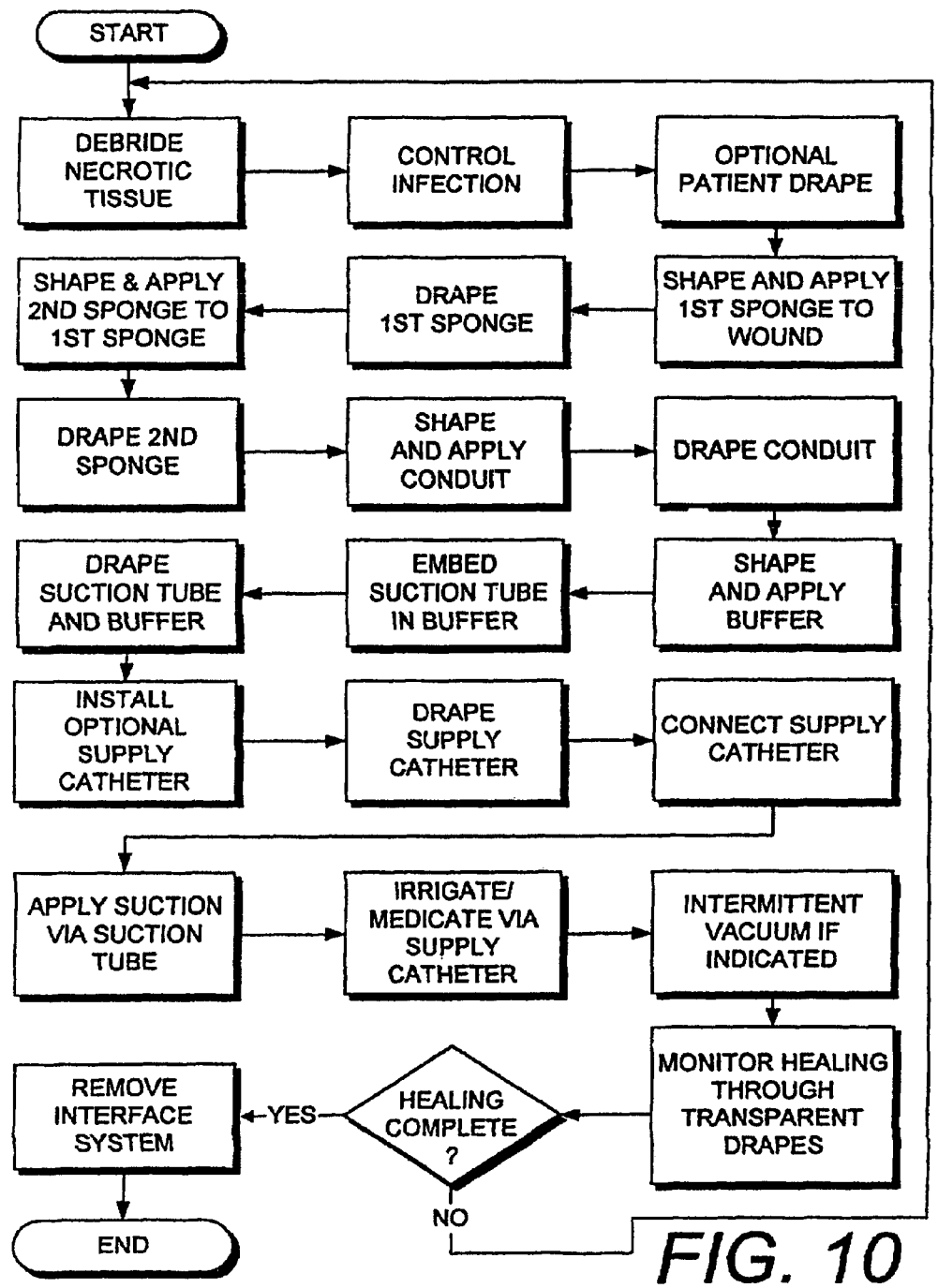
FIG. 10 is a flow diagram of a vacuum-fixed wound therapy method embodying the present invention.

FIG. 10 shows a wound therapy method embodying the present invention. The method can be performed with one or more of the systems discussed above, including the vacuum-fixed dressings 3, 53, 102, 202 and 302. The method can also be performed with a wide variety of variations on the systems and dressings disclosed above.

VIII. Fifth Modified Embodiment Wound Therapy and Tissue Management System 402

Figure 11:
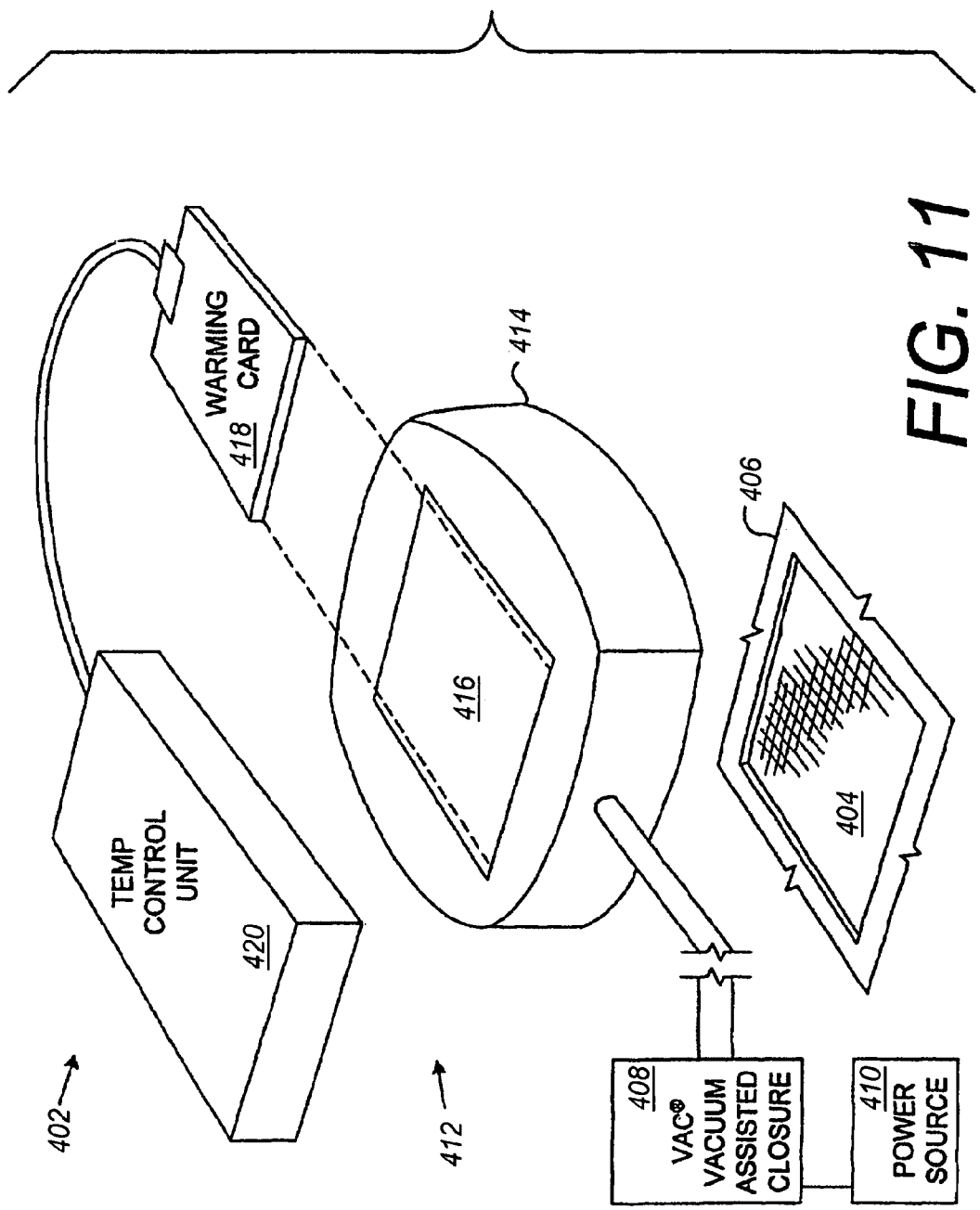
FIG. 11 is an exploded view of a wound treatment system with vacuum, heat and fluid assistance.

FIG. 11 shows a wound therapy and tissue management system 402 comprising a fifth modified embodiment of the present invention. The system 402 includes a dressing 404 placed on a wound 406. Any of the dressing systems discussed above can be utilized. The enclosure 414 is placed over the wound site 406 and includes an opening 416 extending therethrough and adapted for receiving a warming card 418 in covering relation thereover. The warming card 418 is operationally connected to a temperature control unit 420. A vacuum assisted closure unit 408 is fluidically connected to the enclosure 414 by a suitable suction tube and in turn is connected to a power source 410.

In operation, the warming card 418 is heated and raises the temperature within the enclosure 414 to promote healing. The vacuum assisted closure 408 functions as described above to remove effluent and to promote healing in cooperation with the warming card 418. Warming cards and other components for use in connection with this embodiment of the invention are available from Augustine Medical Products, Inc.

IX. Sixth Modified Embodiment Wound Therapy and Tissue Management System 502

Figure 12:
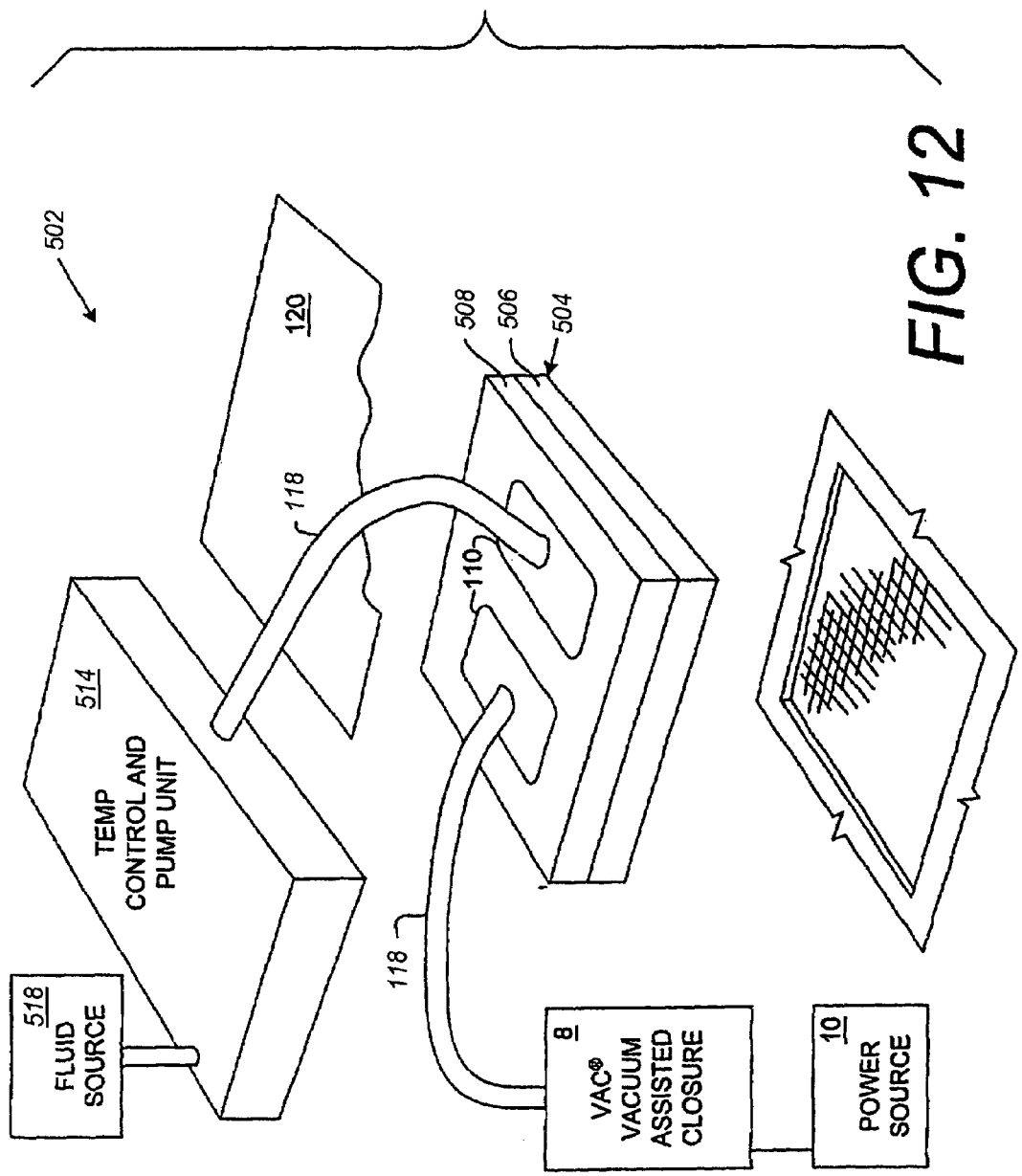
FIG. 12 is an exploded view of another wound treatment system with vacuum, heat and fluid assistance.

FIG. 12 shows a wound therapy and tissue management system 502 comprising a sixth modified embodiment of the present invention. The system 502 is similar to the system 402 described above. A composite dressing 504 is comprised of first and second layers 506, 508. A fluid source 518 communicates with a temperature control and pump unit 514 and provides influx to the system 502.

X. Seventh Modified Embodiment Wound Therapy and Tissue Management System 602

Figure 13:
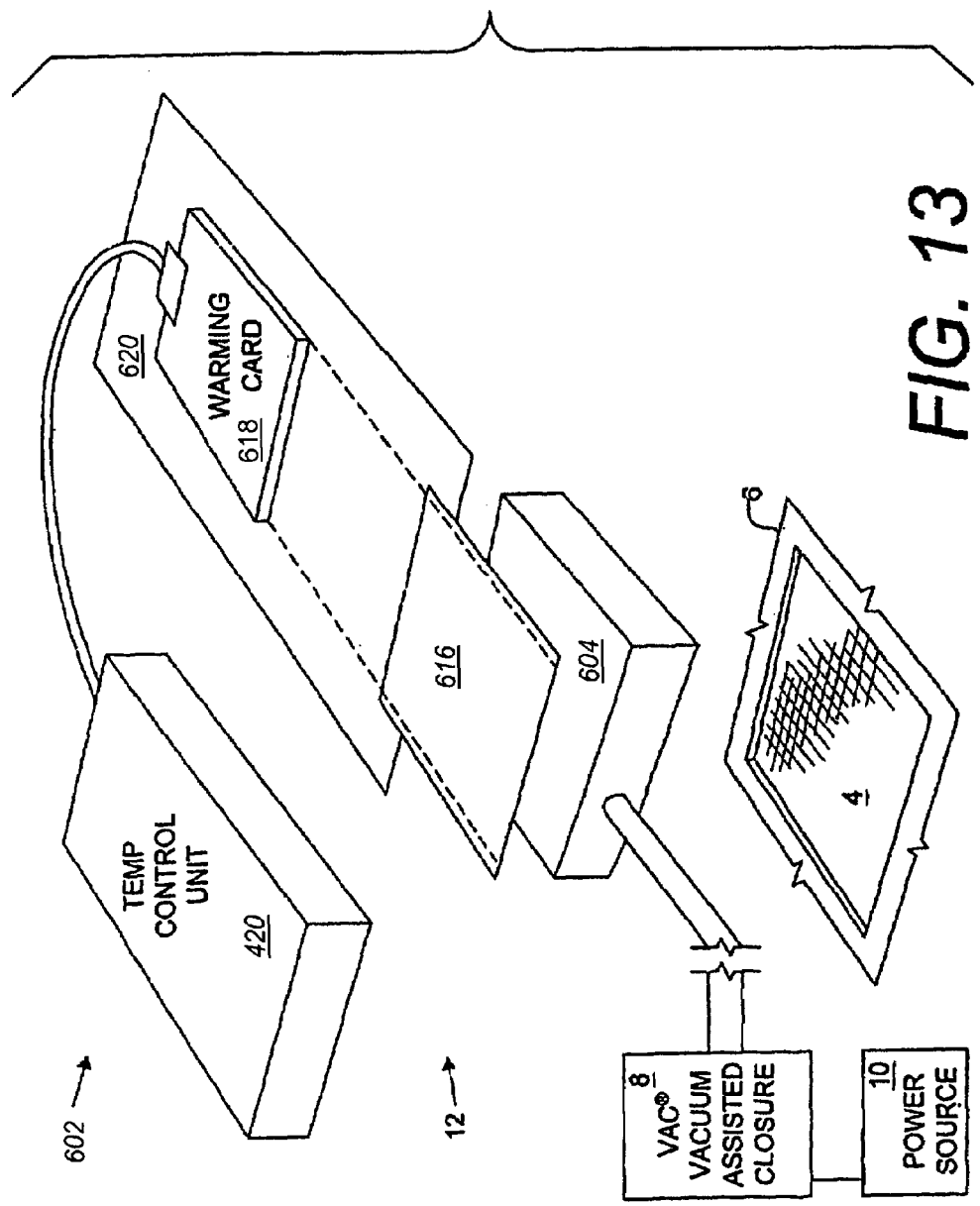
FIG. 13 is an exploded view of yet another wound treatment system with vacuum, heat and fluid assistance.

FIG. 13 shows a wound therapy and tissue management system 602 comprising a seventh modified embodiment of the present invention. The system 602 is similar to the systems 402 and 502 described above. A transfer element 604 is covered by a drape 620, which mounts a film 616 adapted for receiving a warming card 618.

XI. Test Data

Figure 14C:
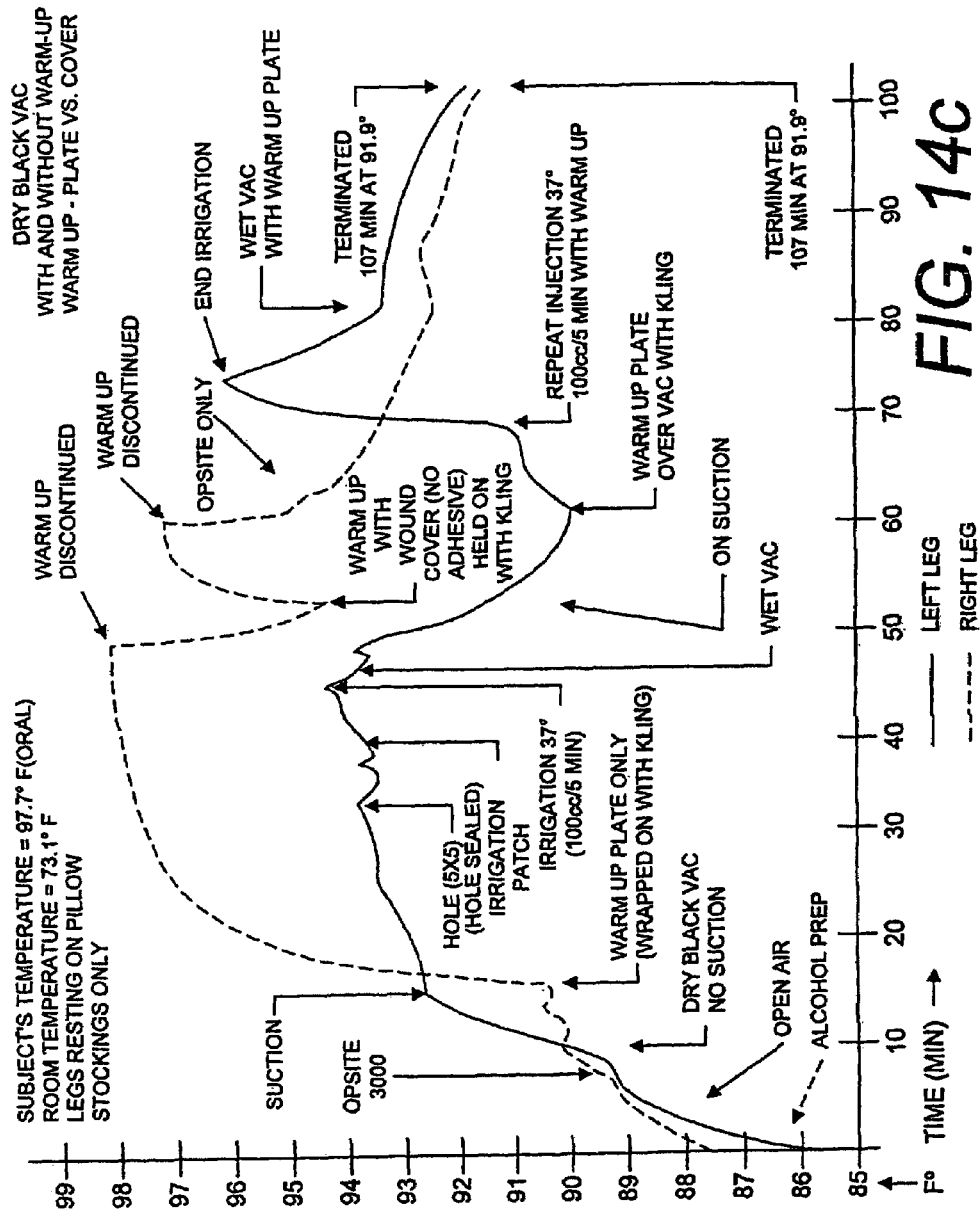
Figure 14D:
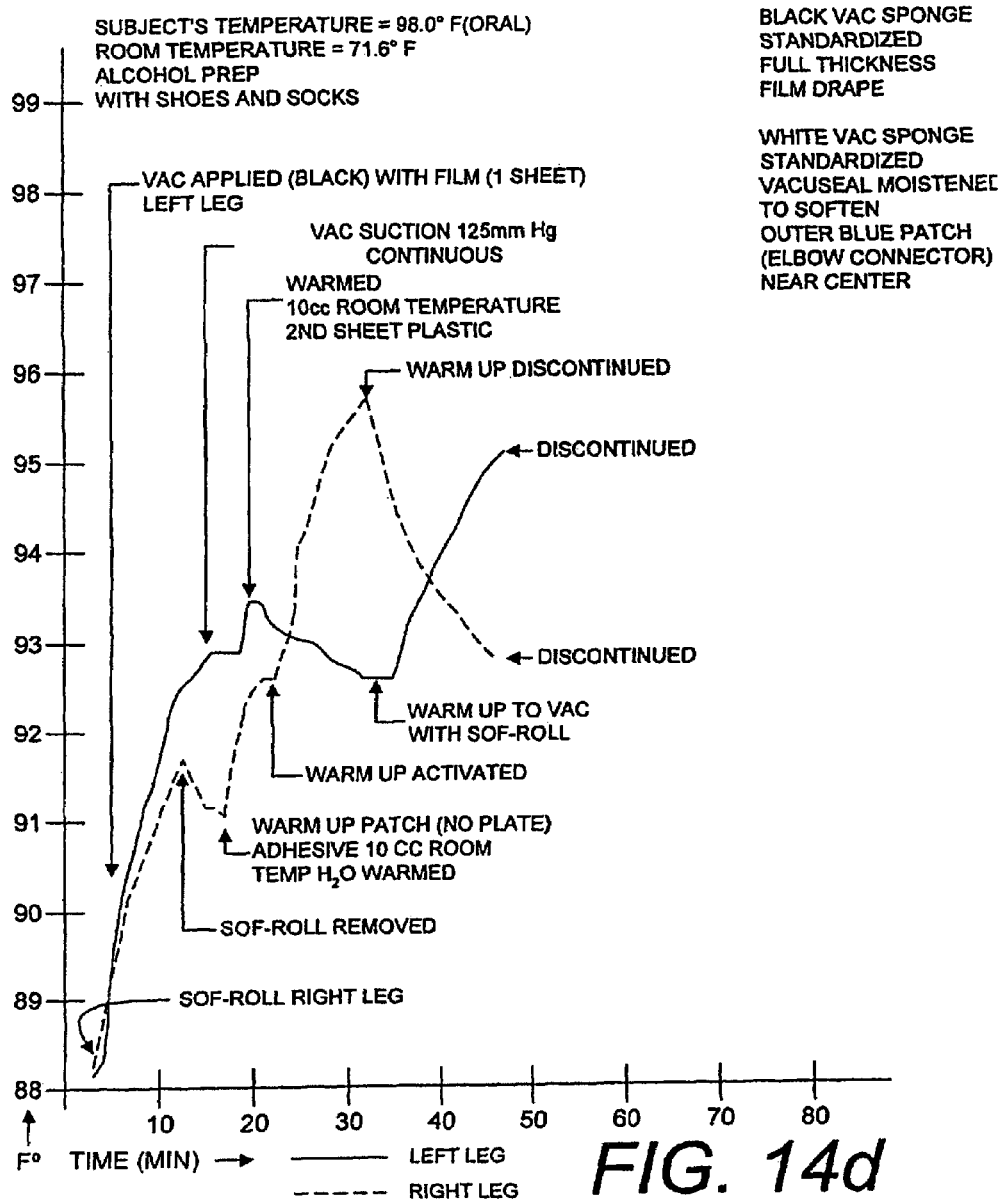

FIGS. 14a–14d shows the results of tests performed with the dressing systems and methodologies discussed above and variations thereon. FIG. 14a shows system performance (time and temperature) with a dry PUE hydrophobic sponge material. FIG. 14b shows system performance with a wet PVA hydrophilic sponge material. FIG. 14c shows performance with an irrigated PUE hydrophobic sponge material with a warm-up plate (heating card) and a cover. FIG. 14d shows system performance with both PUE hydrophobic sponge material and PVA hydrophilic sponge material.

XII. Wound Therapy and Tissue Management System 702

Figure 15:
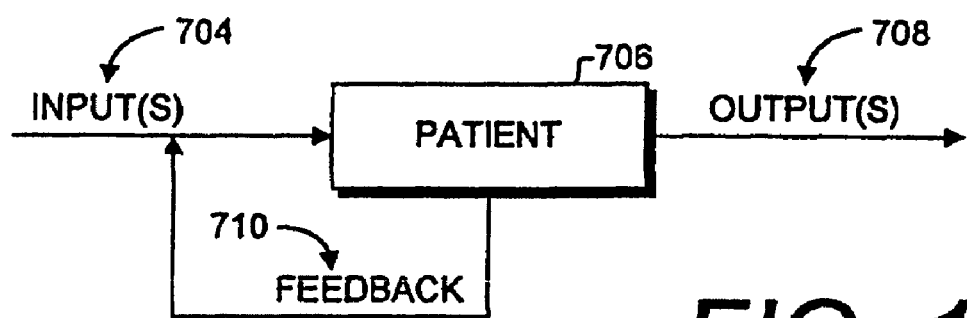
FIG. 15 is a block diagram of a wound therapy and tissue management system comprising an eighth alternative embodiment of the present invention.
Figure 16:
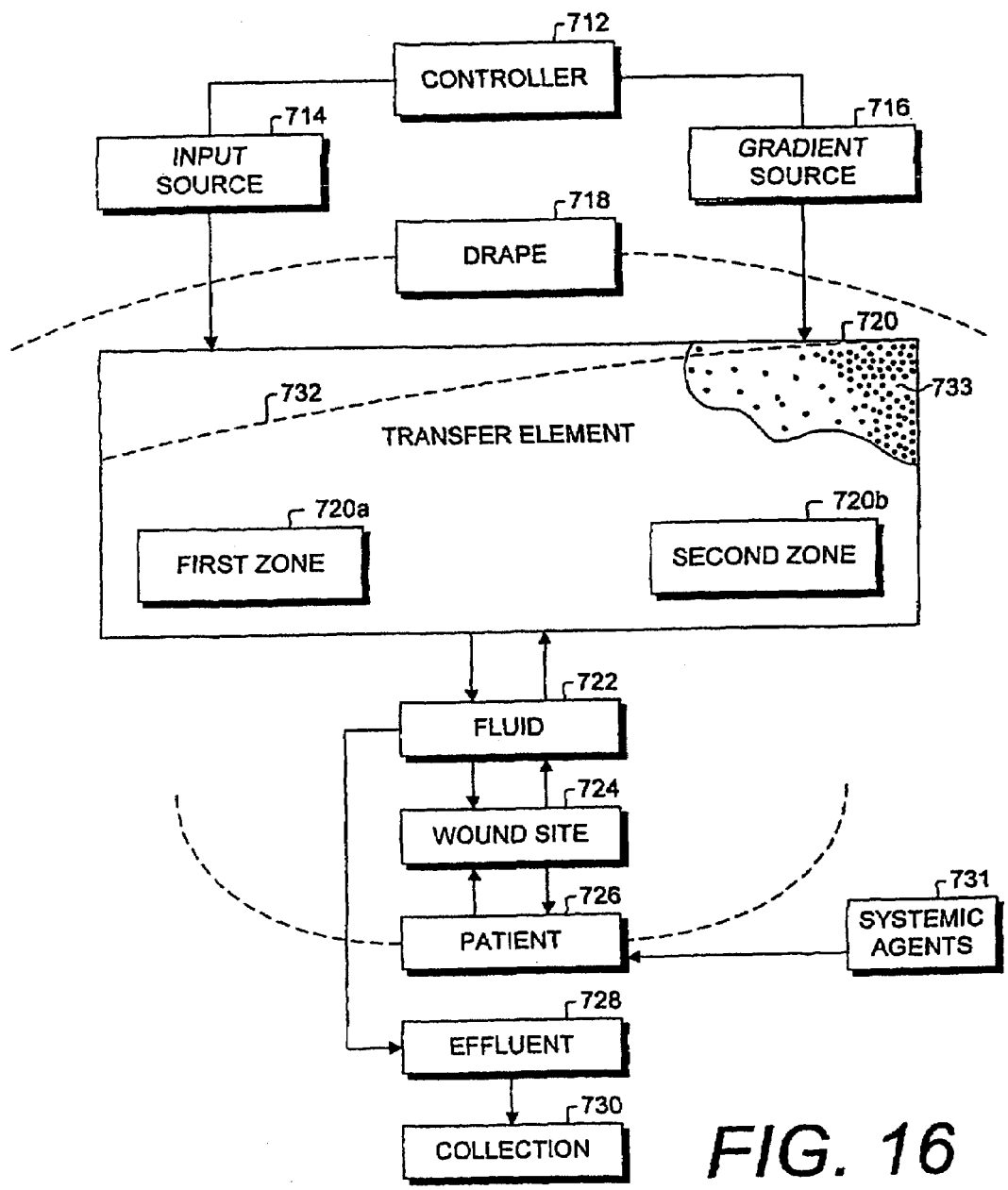
FIG. 16 is a schematic diagram of the eighth alternative embodiment wound therapy and tissue management system.

FIGS. 15 and 16 show a wound therapy and tissue management system 702 comprising an eighth modified embodiment of the present invention. The system 702 is shown schematically in FIG. 15 and consists of inputs 704, the patient 706, outputs 708 and a feedback loop 710. The inputs 704 can comprise virtually any matter or energy deemed appropriate for the treatment protocol by the healthcare practitioner. For example, various irrigation fluids, growth factors, antibiotics, anesthetics, etc. can be input to the patient 706. Still further, the inputs can comprise various forces and energy forms whereby a matter/energy gradient is established with respect to the patient 706.

For example, negative pressure from a suitable vacuum source (such as a VAC unit available from Kinetic Concepts, Inc. of San Antonio, Tex.) can be an input for creating a negative pressure gradient across the system. Likewise, positive pressure from a suitable fluid pump can be input to establish a positive pressure gradient across the system. Other forces can provide electromagnetic, electrical, mechanical and thermal gradients.

The system 702 monitors performance of the patient 706 and controls the inputs 704 interactively in response thereto. Parameters which could be monitored for feedback purposes included moisture levels, temperature, bacteria levels, fluid pressure, etc. The presence or absence of particular elements and compounds can also be sensed, monitored and acted upon. For example, is widely known that oxygen is an important factor in wound healing. Studies have shown that reepithelialization and collagen production are best achieved by varying the oxygen supply. Thus, the oxygen level within the enclosed, wound site environment can be monitored and the oxygen levels therein either increased or decreased as necessary to promote healing. Other controllable parameters include the pH factor and the moisture concentration of the wound environment. Various suitable monitoring means can be employed, including electronic sensors, visual indicators, color-change substances, etc.

The output from the patient can consist of fluid, such as effluent from the wound site, irrigation fluid removed in the process of flushing the wound site, and other matter and energy. An important function of the system is the removal of toxins and bacteria, which can be flushed from the wound site in a liquid or fluid solution.

FIG. 16 is a block diagram of the system 702, showing the components thereof in greater detail. A programmable controller 712 can be preprogrammed to operate the system according to predetermined protocols. The controller 712 is connected to and controls the operation of the input source 714 and the gradient source 716. The input source 714 can comprise any suitable matter or energy for input to the system 702, including various fluids, medications, thermal energy, mechanical forces, temperature, etc., as discussed above. The gradient source is likewise unlimited. For example, pressure gradients (both positive and negative) are particularly suitable for controlling the operation of the system 702 for draining wounds. Other types of gradients include temperature, osmotic, oncotic, pH, oxygen demand, bacteria concentrations, etc., as discussed above.

A gradient source 716 can comprise any suitable device for establishing a gradient. For example, a vacuum source can be utilized for creating a negative pressure gradient. A pump can be utilized for creating a positive pressure gradient. A drape 718 is placed in covering relation over a transfer element 720. The drape 718 can comprise any of the film materials discussed above and can be permeable, semi-permeable or impervious.

The transfer element 720 includes a first zone 720a with a first set of fluid flow characteristics and a second zone 720b with a second set of fluid flow characteristics. Such fluid flow characteristics can be a function of material, thickness, porosity, permeability, and sponge material attraction to proteins, fat cells and other substances. The zones 720a,b can be formed by providing layers of the material, by providing varying thicknesses, by interspersing a first material within a second material in predetermined configurations, etc. Still further, the first and second zones can be formed by subjecting the transfer element 720 to an electromagnetic field.

The first and second zones 720a,b can also be formed by varying the density of the transfer element 720, as indicated by the dashed line 732 (FIG. 16). Line 732 represents compressed material (e.g., foam) along one edge and expanded material in the second zone 720b. Such density gradients can be achieved by compressing the material or by heat-setting same in a manufacturing process. Transfer element 720 edges can also be compressed when the dressing is applied to achieve a desired density gradient. Material thickness can also be utilized to provide a flow coefficient gradient. In this case line 732 could represent a tapering of the transfer element 720 across the first and second zones 720a, 720b. A marbling effect with a material concentration gradient is shown at 733, with greater concentration along an edge and decreasing concentration towards interior portions of the transfer element 720, or vice-versa. Constructing the first and second zones 720a, 720b of different materials with different respective flow coefficients could also achieve a desired flow gradient.

Medications and other substances can be applied to the transfer element materials to alter the flow characteristics thereof. Systemic agents 731 can be administered to the patient 726.

Fluid 722 can be introduced into the wound site 724 from the inputs 714 and its flow pathways can be controlled by the gradient source 716. For example, sponge materials with different flow characteristics can be configured to direct fluid (either gas or liquid) in predetermined flow patterns through the transfer element 720. Effluent 728 from the patient 726 is withdrawn from the wound site 724 and evacuated to a collection receptacle 730.

XIII. Wound Therapy and Tissue Management Methodology

Figure 17:
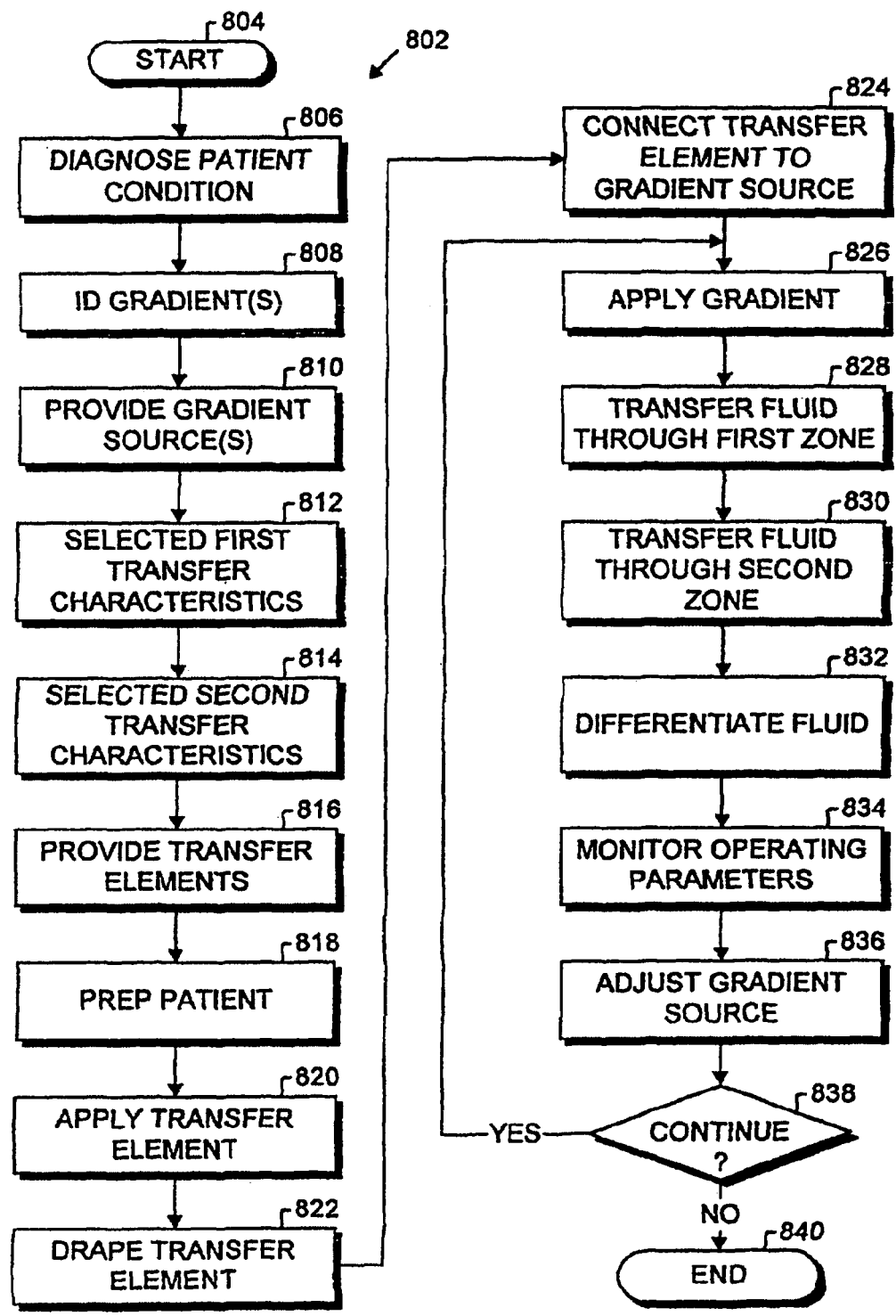
FIG. 17 is a flowchart of a wound and therapy and tissue management methodology embodying the present invention.
Figure 18:
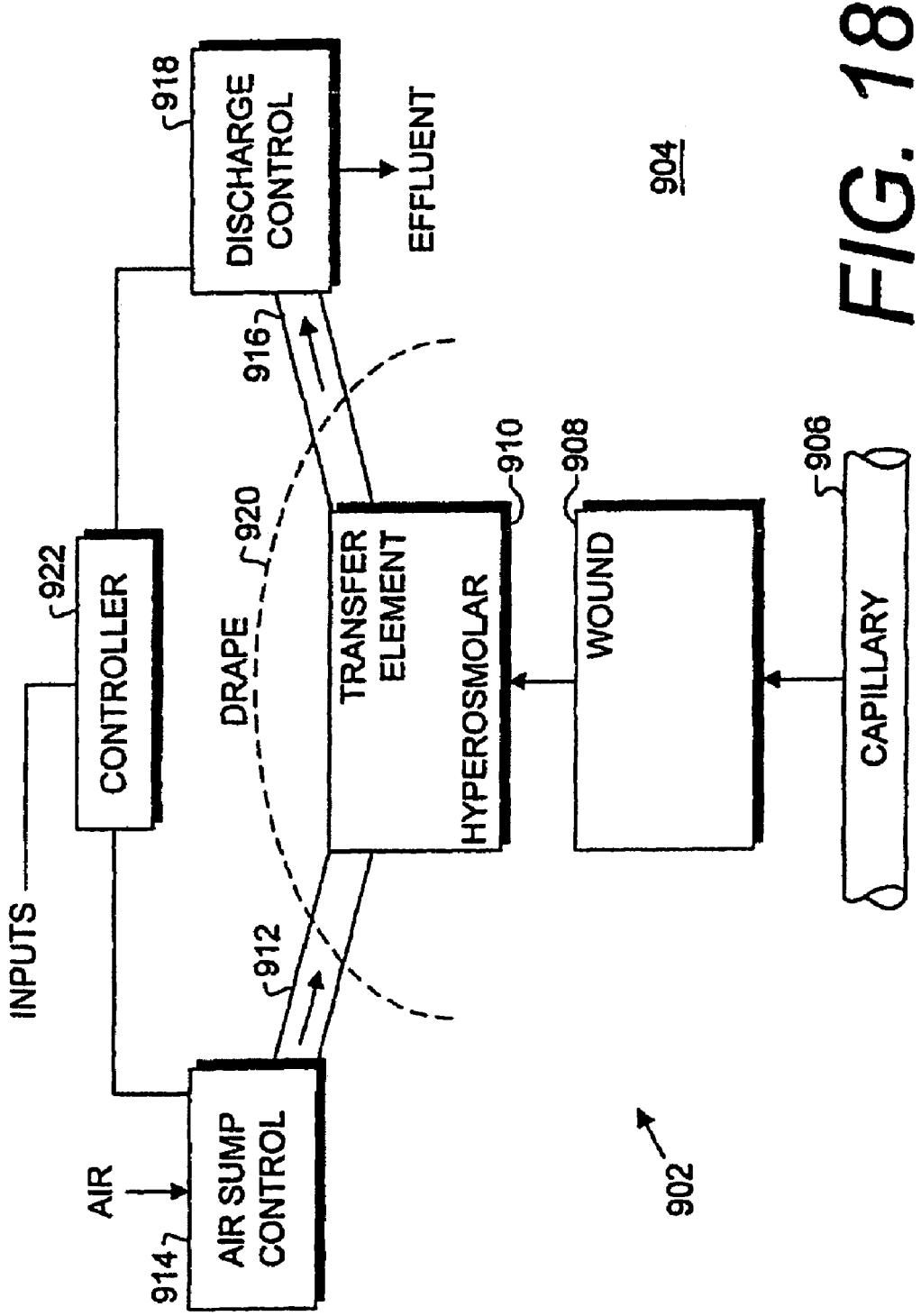
FIG. 18 is a block diagram of a wound therapy and tissue management system comprising a ninth alternative by the present invention.

FIG. 17 shows a flowchart for a wound therapy and tissue management methodology embodying the president mentioned. From Start 804, the method proceeds to Diagnose Patient Condition 806. Based on the diagnosis, a treatment protocols selected. The protocol includes an identification of a gradients to be controlled by the methodology. For example, protocols involving vacuum-assisted wound drainage will generally include a negative pressure gradient. Additional possible gradients are discussed above. It will be appreciated that virtually unlimited combinations of gradients can be formed in the system 702. Moreover, the timing of the gradient control can be varied as needed to achieve desired treatment results. For example, collagen production and reepithelialization can be promoted by hyperbaric oxygen treatment procedures, such as alternating elevated and reduced oxygen concentrations. Suction/compressive pressures can also be alternated to stimulate tissue growth.

Gradient sources are provided at 810 and can comprise vacuum/suction, fluids, medications, oxygen and various other matter and energy. Gradients can also be formed utilizing energy sources, such as thermal, mechanical force, etc. First and second transfer characteristics are selected at 812, 814 respectively. A transfer element(s) is provided at 816 and includes the transfer characteristics selected at 812, 814. The patient is prepared at 818. Patient preparations can include any suitable medical procedures, such as debriding the wound, etc.

The transfer element is applied at 820 and draped at 822. The transfer element is connected to a gradient source at 824 and the gradient is applied at 826. Fluid is transferred through the first transfer element zone at 828 and through the second transfer element zone at 830. It will be appreciated that such transfer zones can be adapted for directing the fluid along certain pathways to achieve desired results, such as evacuation of exudates. The fluid is differentiated (e.g., liquids, gases or liquids and gases are separated) at 832.

The operating parameters are monitored at 834 and the gradient source(s) are adjusted accordingly add 836. Thereafter a "Continue?" decision box 838 is reached. If affirmative, the method returns to Apply Gradient 826 and operation continues with the adjusted gradient parameters. A negative decision at 838 leads to a termination of the procedure (i.e., "End") at 840.

XIV. Osmotic Gradient Wound Therapy and Tissue Management System 902 and Methodology FIGS. 18–21 show a wound therapy and tissue management system 902 and methodology utilizing a controlled osmotic gradient. A patient 904 includes capillaries 906 which provide fluid, such as serum and blood, to a wound 908. Such fluid passes to the transfer element 910. An air sump control 914 communicates with the transfer element 910 through an air sump conduit 912. A discharge control 918 communicates with the transfer element 910 through a discharge conduit 916. The controls 914, 918 are interactively controlled by a controller 922, which is adapted to receive control input signals. Such input signals can comprise, for example, preprogrammed inputs, feedback signals (FIG. 15), etc. The input signals can originate at sensors associated with the system 902 and with the patient 904. Such inputs can effectively control the osmotic gradient to achieve desired fluid, solvent and solute (e.g., toxin) transfers. For example, the primary external substance input can comprise relatively dry ambient air. Air movement through the system 902 tends to collect moisture for discharge as water vapor.

The system 902 is covered by a drape 920, which can comprise various semi-permeable and impervious materials as required by fluid flow considerations and various applications. For example, an impervious drape 920 tends to block air from the system 902 and permit entry of same only through the air sump control 914.

Figure 19:
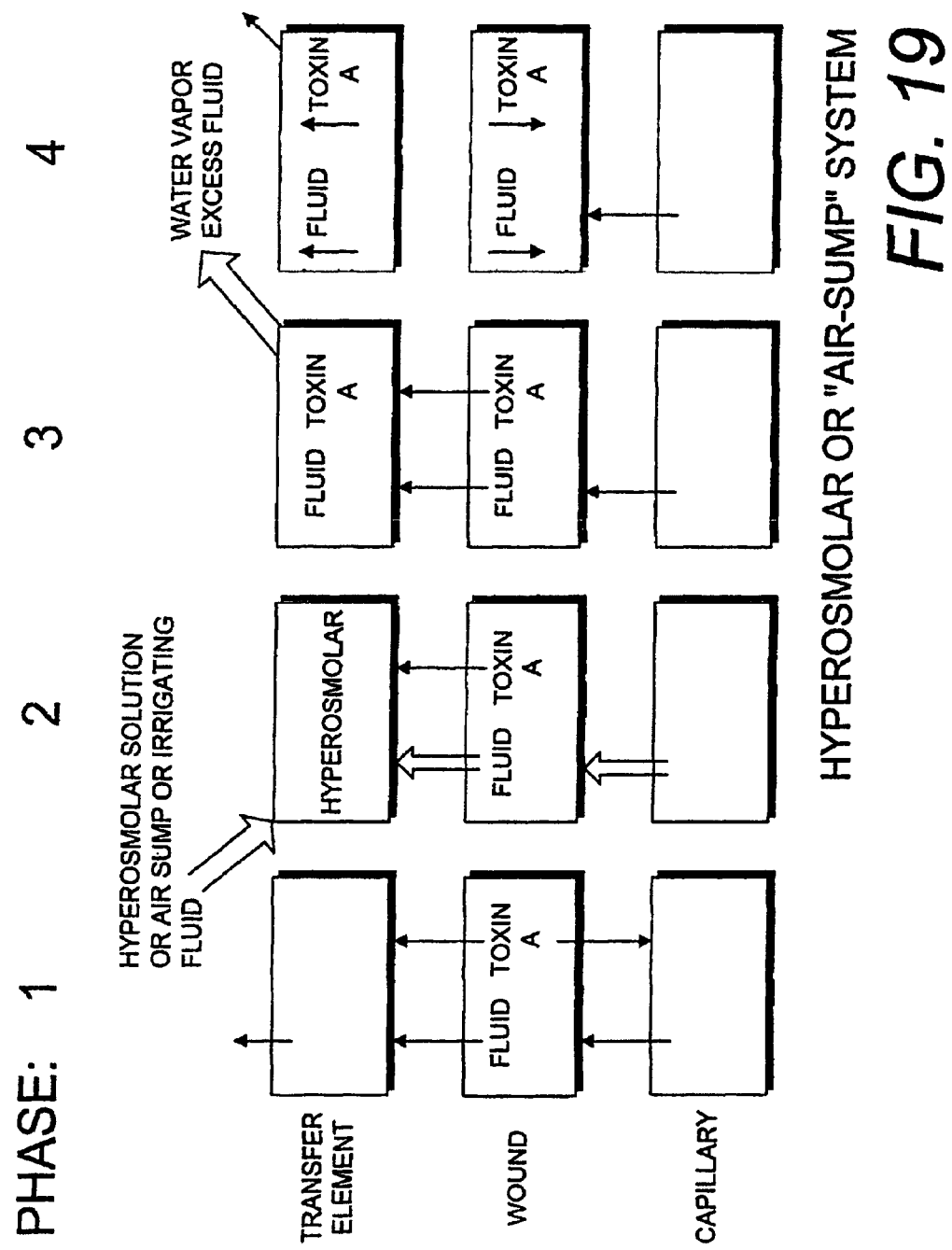
FIG. 19 is a diagram showing various phases in a hyper-osmolar or air-sump system embodying the present invention.

FIG. 19 shows a hypersomolar or air-sump system. Phase 1 represents a steady-state or increasing-toxin A condition and a concomitant increasing movement of toxin A back into the patient. In phase 2 a hyperosmolar solution or air sump is introduced. This gradient draws fluid from the capillaries to replace the fluid moved out of the wound into the transfer element carrying toxin A with it and decreasing movement of toxin A into the patient. Alternatively or in addition, warmed irrigating fluid can be introduced into the transfer element in phase 2. The advantages of warming the transfer element and wound site in this manner include vasodilation, increase in cell motility and an increase in phagocytosis. For example, irrigating fluid warmed to approximately 40 degrees centigrade has been shown to remove the inhibitory effect of chronic wound fluid on cell culture motility and proliferation.

In phase 3, ongoing administration of this gradient continues these fluxes as water vapor is removed and dry air is sumped. In phase 4 is results in a new steady-state condition with lower levels of toxin A in the wound (and the patient) and increased fluid and toxin A in the transfer element that is continuously evacuated.

Figure 20:
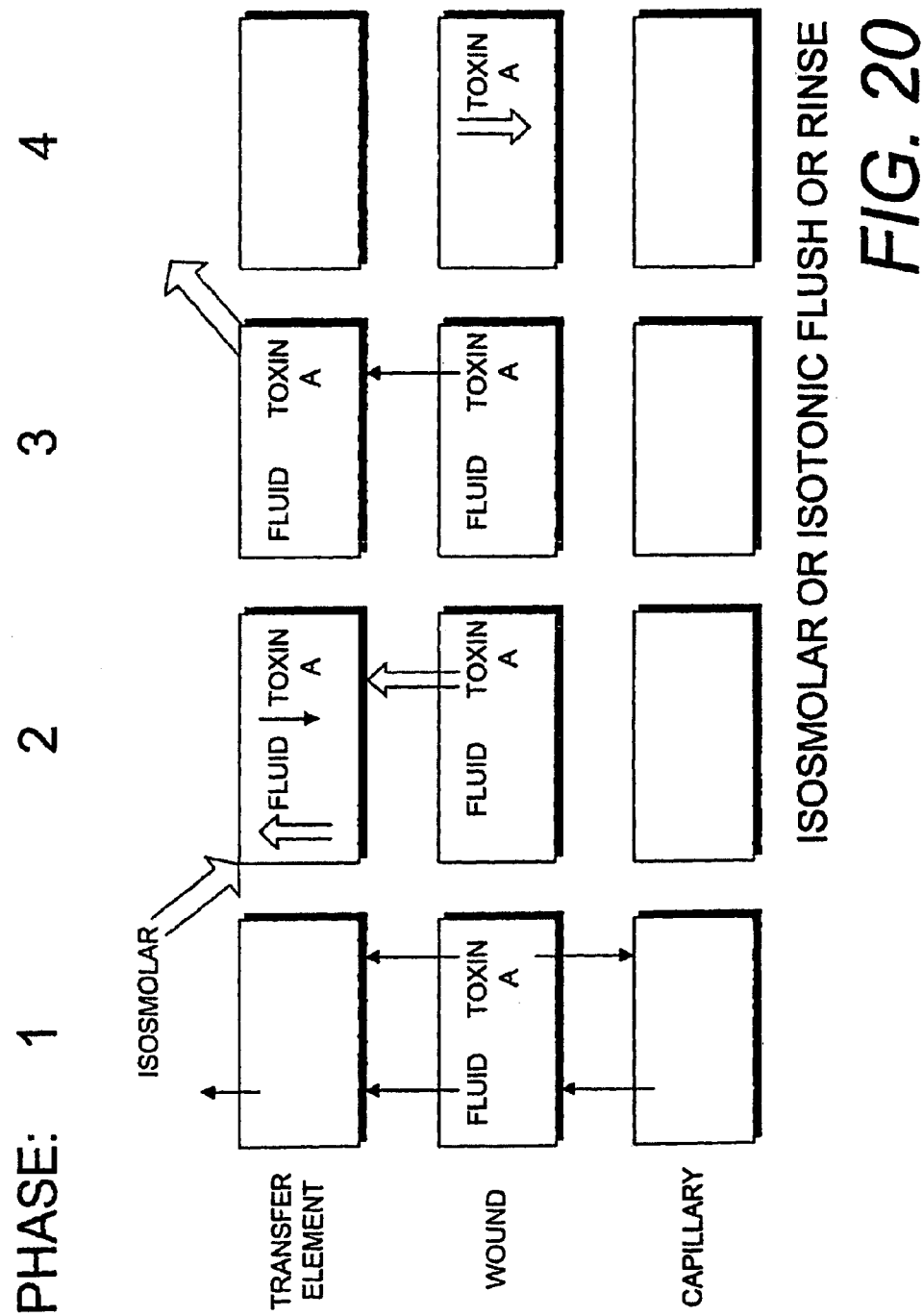
FIG. 20 is a diagram showing various phases in an osmolar or isotonic flush or rinse system embodying the present invention.

FIG. 20 shows an isosmotic or isotonic flush or rinse methodology. In phase I there is a steady-state (or increasing toxin A level) condition with fluid (liquids) moving out from the wound to the transfer element being replaced by serum exudate from the capillary. Evaporative loss from the transfer element is kept to a minimum by application of a drape material.

In phase 2, an isomotic rinse is introduced, increasing the fluid content of the transfer element and decreasing the concentration of toxin A, enabling a diffusion of toxin A from the wound into the transfer element. In phase 3, as this fluid is withdrawn, it also removes toxin A, enabling a continued diffusion of toxin A out of the wound. In phase 4, the resulting condition is fluid equilibrium and decreased concentration of toxin A in the wound. As this situation reverts to phase 1, the flush or rinse is repeated at intervals.

FIG. 21 shows a hypo-osmolar or heavy drape system. In phase 1 steady-state conditions generally exist with some evaporative loss of fluid (water vapor). In phase 2, small amounts of hypo-osmolar fluid are introduced, or a cover/drape is placed over the transfer element with a heavy drape completely blocking evaporative loss, thus adding "free water" to the system. This reverses the outward flow of fluid from the wound.

In phase 3 this increased fluid in the wound allows the total amount of toxin A to also accumulate in the wound. In phase 4 this increase of fluid and toxin A in the wound without any egress produces movement of fluid (edema) and toxins (cellulitis) back into the patient and into the lymphatics.

CONCLUSION

It is to be understood that while certain forms of the present invention have been illustrated and described herein, it is not to be limited to the specific forms or arrangement of parts described and shown.

Furthermore, it should be appreciated that continuatins, divisionals, and continuations-in-part applications depending from this specification may be pending at the time this patent issues, the claims of which may encompass embodiments and applications that are broader than the claims appended herein. Accordingly, embodiments or elements disclosed in the specification but not literally claimed in the appended claims, if any, should not be presumed to be dedicated to the public.

What is claimed and desired to be secured by Letters Patent is as follows:

1. A fluid-differentiating wound therapy and tissue management system, which comprises:
   a) a fluid transfer element including:
      1) a non-attaching patient contact surface;
      2) a first zone with a first fluid transfer coefficient;
      3) a second zone with a second fluid transfer coefficient different from said first fluid transfer coefficient, said second zone being located adjacent to said first zone; and
      4) a predetermined fluid flow path through said element guided by said fluid transfer coefficient differential between said first and second zones;
   b) a cover placed over said transfer element in contact therewith and including adhesive adapted for adhering said cover to a patient around the perimeter of said fluid transfer element;
   c) a gradient source for creating a gradient across said transfer element whereby fluids are moved through said transfer element;
   d) an effluent conduit connected to said transfer element and adapted for discharging effluent from the system; and e) said predetermined fluid flow path being towards said effluent conduit.

2. The system of claim 1 with a pressure gradient source.

3. The system of claim 2 with the pressure gradient source comprising a vacuum source.

4. The system of claim 2 with a pump.

5. The system of claim 1 with an inlet conduit.

6. The system of claim 1 with a draped material cover.

7. The system of claim 1 with first and second layers of sponge material.

8. The system of claim 1 with fluid flow characteristic zones.

9. The system of claim 8 with intermingled sponge material.

10. The system of claim 1 with a temperature gradient.

11. The system of claim 1 with an oxygen concentration gradient.

12. The system of claim 1 with a fluid concentration gradient.

13. The system of claim 1 with an oncotic gradient.

14. The system according to claim 1 wherein said gradient comprises an osmotic gradient.

15. The system of claim 1 with a programmable controller.

16. The system of claim 15 wherein the controller is programmed.

17. The system of claim 1 with a multiple-passage conduit.

18. The system of claim 1 with an input to the transfer element.

19. The system of claim 1 with a monitor and a feedback loop.

20. A fluid-differentiating wound therapy and tissue management method, which includes steps of:
   a) providing a fluid transfer element with a patient contact surface, a first zone with a first fluid transfer coefficient and a second zone located adjacent to said first zone with a second fluid transfer coefficient different from said first fluid transfer coefficient;
   b) providing a predetermined flow path through said element guided by said liquid fluid transfer coefficient differential between said first and second zones;
   c) mounting said transfer element on said patient in communication with a wound site;
   d) covering said transfer element with a cover;
   e) releasably adhering said cover to said patient around said wound site;
   f) providing a gradient source;
   g) connecting said gradient source to said transfer element;
   h) establishing a gradient across said transfer element;
   i) providing an effluent conduit and directing said predetermined fluid flow path towards said effluent conduit;
   j) connecting said effluent conduit to said transfer element and to said gradient source;
   k) differentiating the fluid within the enclosure; and
   l) draining liquid from said transfer element.

21. A fluid-differentiating wound therapy and tissue management system, which comprises:
   a) a fluid transfer element including:
      1) a patient contact surface;
      2) a first zone with a first fluid transfer coefficient;
      3) a second zone with a second fluid transfer coefficient different from said first fluid transfer coefficient, said second zone being located adjacent to said first zone; and
      4) a predetermined fluid flow path through said element guided by said fluid transfer coefficient differential between said first and second zones;
   b) a cover placed over said transfer element in contact therewith and adapted for contact with the patient around the perimeter of said fluid transfer element;
   c) a gradient source for creating an oncotic gradient across said transfer element; and
   d) an effluent conduit connected to said transfer element and adapted for discharging effluent from the system.

* * * * *